United States Patent
Kent et al.

(10) Patent No.: US 12,258,620 B2
(45) Date of Patent: Mar. 25, 2025

(54) ALLELE-SPECIFIC DESIGN OF COOPERATIVE PRIMERS FOR IMPROVED NUCLEIC ACID VARIANT GENOTYPING

(71) Applicant: CO-DIAGNOSTICS, INC., Salt Lake City, UT (US)

(72) Inventors: Jana Kent, Salt Lake City, UT (US); Masen Chad Christensen, Salt Lake City, UT (US); Brent Coleman Satterfield, Wichita Falls, TX (US)

(73) Assignee: CO-DIAGNOSTICS, INC., Salt Lake City, UT (US)

( * ) Notice: Subject to any disclaimer, the term of this patent is extended or adjusted under 35 U.S.C. 154(b) by 764 days.

(21) Appl. No.: 17/279,825

(22) PCT Filed: Sep. 25, 2019

(86) PCT No.: PCT/US2019/052957
§ 371 (c)(1),
(2) Date: Mar. 25, 2021

(87) PCT Pub. No.: WO2020/068983
PCT Pub. Date: Apr. 2, 2020

(65) Prior Publication Data
US 2021/0395800 A1 Dec. 23, 2021

Related U.S. Application Data

(60) Provisional application No. 62/736,094, filed on Sep. 25, 2018.

(51) Int. Cl.
*C12Q 1/6827* (2018.01)

(52) U.S. Cl.
CPC .................................. *C12Q 1/6827* (2013.01)

(58) Field of Classification Search
CPC ..................................................... C12Q 1/6827
See application file for complete search history.

(56) References Cited

U.S. PATENT DOCUMENTS

| | | | |
|---|---|---|---|
| 3,687,808 A | 8/1972 | Merigan, Jr. et al. |
| 4,469,863 A | 9/1984 | Ts'o et al. |
| 4,476,301 A | 10/1984 | Imbach et al. |
| 4,845,205 A | 7/1989 | Dinh et al. |
| 4,981,957 A | 1/1991 | Lebleu et al. |
| 5,023,243 A | 6/1991 | Tullis |

(Continued)

FOREIGN PATENT DOCUMENTS

| | | |
|---|---|---|
| CN | 112831600 | 5/2021 |
| WO | 98/22489 | 5/1998 |

(Continued)

OTHER PUBLICATIONS

Vargas, D.Y. et al. PLOS ONE 11(5):e0156546 (25 pages). May 2016. (Year: 2016).*

(Continued)

*Primary Examiner* — Diana B Johannsen
(74) *Attorney, Agent, or Firm* — Meunier Carlin & Curfman LLC

(57) ABSTRACT

Disclosed herein is a method of synthesizing a target nucleic acid preferentially relative to a nucleic acid with one or more nucleotides that differ from the target nucleic acid. Also disclosed are systems and kits for the same.

15 Claims, 29 Drawing Sheets

(56) References Cited

U.S. PATENT DOCUMENTS

| | | |
|---|---|---|
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,724 A | 11/1995 | Ahern |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,646,265 A | 7/1997 | McGee |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 6,268,490 B1 | 7/2001 | Imanishi et al. |
| 6,291,669 B1 | 9/2001 | Kwiatkowski et al. |
| 6,294,664 B1 | 9/2001 | Ravikumar et al. |
| 6,670,461 B1 | 12/2003 | Wengel et al. |
| 10,093,966 B2 | 10/2018 | Satterfield |
| 10,704,087 B2 | 7/2020 | Satterfield |
| 2003/0064402 A1 | 4/2003 | Egholm |
| 2009/0098566 A1 | 4/2009 | Notomi et al. |
| 2009/0305264 A1 | 12/2009 | West et al. |
| 2010/0021904 A1 | 1/2010 | Pierce et al. |
| 2010/0055742 A1 | 3/2010 | Nakashima et al. |
| 2011/0020823 A1 | 1/2011 | Burns |
| 2011/0027786 A1 | 2/2011 | Satterfield |
| 2012/0135473 A1 | 5/2012 | Chun et al. |
| 2012/0220468 A1 | 8/2012 | Chun et al. |
| 2014/0038182 A1 | 2/2014 | Satterfield |
| 2017/0247752 A1 | 8/2017 | Satterfield |
| 2018/0363036 A1 | 12/2018 | Satterfield |

FOREIGN PATENT DOCUMENTS

| | | | |
|---|---|---|---|
| WO | 98/39352 | 9/1998 | |
| WO | 99/14226 | 3/1999 | |
| WO | 2002/002817 | 1/2002 | |
| WO | 02/068684 | 9/2002 | |
| WO | 2006/119326 | 11/2006 | |
| WO | 2017/098023 | 6/2017 | |
| WO | WO-2017176852 A1 * | 10/2017 | ............. C12P 19/30 |

OTHER PUBLICATIONS

WikiDoc definition of Upstream and downstream (DNA), 1 page. (Year: 2012).*

Akhras et al. 2007: Hall, Neil. ed. "Connector inversion probe technology: a powerful one-primer multiplex DNA amplification system for numerous scientific applications". PLoS ONE 2 (9): e195.

Englisch et al., Angewandte Chemie, International Edition, 1991, 30, 613.

Gebinoga, M. & Oehlenschlager, F., Comparison of self-sustained sequence-replication reaction systems, European Journal of Biochemistry, 235:256-261, (1996).

Hall, R. H., Alexander Todd, and R. F. Webb. "644. Nucleotides. Part XLI. Mixed anhydrides as intermediates in the synthesis of dinucleoside phosphates." Journal of the Chemical Society (Resumed) (1957): 3291-3296.

Hall, J. G., Eis, P. S., Law, S. M., Reynaldo, L. P., Prudent, J. R., Marshall, D. J., . . . & Lyamichev, V. I. (2000). Sensitive detection of DNA polymorphisms by the serial invasive signal amplification reaction. Proceedings of the National Academy of Sciences, 97(15), 8272-8277.

Hardenbol et al 2003: "Multiplexed genotyping with sequence-tagged molecular inversion probes". Nat Biotechnol 21 (6): 673-678.

Heim, A., Zeuke, S., Grumbach, I. M., & Top, B. (1998). Highly sensitive detection of gene expression of an intronless gene: amplification of mRNA, but not genomic DNA by nucleic acid sequence based amplification (NASBA). Nucleic acids research, 26(9), 2250-2251.

Holland, P. M., Abramson, R. D., Watson, R., & Gelfand, D. H. (1991). Detection of specific polymerase chain reaction product by utilizing the 5'----3'exonuclease activity of Thermus aquaticus DNA polymerase. Proceedings of the National Academy of Sciences, 88(16), 7276-7280.

Ikuta et al., Ann. Rev. Biochem. 53:323-356 (1984).

(56) References Cited

OTHER PUBLICATIONS

Lizardi, P. M., & Kramer, F. R. (1991). Exponential amplification of nucleic acids: new diagnostics using DNA polymerases and RNA replicases. Trends in biotechnology, 9(1), 53-58.
Kwoh, D. Y., Davis, G. R., Whitfield, K. M., Chappelle, H. L., DiMichele, L. J., & Gingeras, T. R. (1989). Transcription-based amplification system and detection of amplified human immunodeficiency virus type 1 with a bead-based sandwich hybridization format. Proceedings of the National Academy of Sciences, 86(4), 1173-1177.
Lesnik, E. A., & Freier, S. M. (1995). Relative Thermodynamic Stability of DNA, RNA, and DNA:RNA Hybrid Duplexes: Relationship with Base Composition and Structure. Biochemistry, 34(34), 10807-10815. doi:10.1021/bi00034a013.
Lindblad-Toh, K., Winchester, E., Daly, M. J., Wang, D. G., Hirschhorn, J. N., Laviolette, J. P., . . . & Lander, E. S. (2000). Large-scale discovery and genotyping of single-nucleotide polymorphisms in the mouse. Nature genetics, 24(4), 381-386.
Little, M. C., Andrews, J., Moore, R., Bustos, S., Jones, L., Embres, C., . . . & Boenisch, M. (1999). Strand displacement amplification and homogeneous real-time detection incorporated in a second-generation DNA probe system, BDProbeTecET. Clinical chemistry, 45(6), 777-784.
Matteucci, Mark Douglas, and M. Ho Caruthers. "Synthesis of deoxyoligonucleotides on a polymer support." Journal of the American Chemical Society 103.11 (1981): 3185-3191.
McGraw, R. A., Steffe, E. K., & Baxter, S. M. (1990). Sequence-dependent oligonucleotide-target duplex stabilities: rules from empirical studies with a set of twenty-mers. BioTechniques, 8(6), 674-678.
Moore, D. F., & Curry, J. I. (1998). Detection and identification of *Mycobacterium tuberculosis* directly from sputum sediments by ligase chain reaction. Journal of clinical microbiology, 36(4), 1028-1031.
Narang, S. A., Brousseau, R., Hsiung, H. M., & Michniewicz, J. J. (1980). [61] Chemical synthesis of deoxyoligonucleotides by the modified triester method. In Methods in Enzymology (vol. 65, pp. 610-620). Academic Press.
Nazarenko, I. A., Bhatnagar, S. K., & Hohman, R. J. (1997). A closed tube format for amplification and detection of DNA based on energy transfer. Nucleic acids research, 25(12), 2516-2521.
Nielsen, P. E., Egholm, M., & Buchardt, O. (1994). Peptide nucleic acid (PNA). A DNA mimic with a peptide backbone. Bioconjugate chemistry, 5(1), 3-7.
Nielsen, P., Egholm, M., Berg, R., & Buchardt, O. (1991). Sequence-selective recognition of DNA by strand displacement with a thymine-substituted polyamide. Science, 254(5037), 1497-1500. doi:10.1126/science.1962210.
Nilsson et al. 1994: "Padlock probes: circularizing oligonucleotides for localized DNA detection". Science 265 (5181): 2085-2088.
Pless, R.C., et al., "Solid support synthesis of oligothymidylates using phosphorochloridates and 1-alkylimidazoles," Nucleic Acids Research, vol. 2, No. 6, Jun. 1975, pp. 773-786.
Letsinger, R.L., et al., "Synthesis of Thymidine Oligonucleotides by Phosphite Triester Intermediates," Journal of the American Chemical Society, vol. 98, 1976, pp. 3655-3661.
Iyer, R.P., et al., "3H-1,2-Benzodithiole-3-one 1,1-dioxide as an improved sulfurizing reagent in the solid-phase synthesis of oligodeoxyribonucleoside phosphorothioates," J. Am. Chem. Soc., vol. 112, No. 3, 1990, pp. 1253-1254.
Rychlik, W., et al., "Optimization of the annealing temperature for DNA amplification in vitro," Nucleic Acids Research, vol. 18, No. 21, 1990, pp. 6409-6412.
Beaucage, S.L., et al., "Deoxynucleoside Phosphoramidites—A New Class of Key Intermediates for Deoxypolynucleotide Synthesis," Tetrahedron Letters, vol. 22, No. 20, 1981, pp. 1859-1862.
Sanghvi, Y.S., "Heterocyclic Base Modifications in Nucleic Acids and Their Applications in Antisense Oligonucleotides," Chapter 15, Antisense Research and Applications, CRC Press, 1993, pp. 273-288.

Schweitzer, B., & Kingsmore, S. (2001). Combining nucleic acid amplification and detection. Current Opinion in Biotechnology, 12(1), 21-27. doi:10.1016/s0958-1669(00)00172-5.
Thelwell, Nicola, et al. "Mode of action and application of Scorpion primers to mutation detection." Nucleic acids research 28.19 (2000): 3752-3761.
Walker, G.T., et al., "Isothermal in vitro amplification of DNA by a restriction enzyme/DNA polymerase system," Proc. Natl. Acad. Sci. USA, vol. 89, 1992, pp. 392-396.
Whelan, A.C., et al., "Direct Genotypic Detection of *Mycobacterium tuberculosis* Rifampin Resistance in Clinical Specimens by Using Single-Tube Heminested PCR," Journal of Clinical Microbiology, vol. 33, No. 3, 1995, pp. 556-561.
Wylie, J.L., et al., "Comparative Evaluation of Chlamydiazyme, PACE 2, and AMP-CT Assays for Detection of Chlamydia trachomatis in Endocervical Specimens," Journal of Clinical Microbiology, vol. 36, No. 12, 1998, pp. 3488-3491.
Extended European Search report issued for European Application No. 19866029, dated May 31, 2022.
Satterfield, Brent C. "Cooperative Primers: 2.5 Million-Fold Improvement in the Reduction of Nonspecific Amplification." The Journal of Molecular Diagnostics 16.2 (2014): 163-173.
Kandimalla, Ekambar R., et al. "Design, biochemical, biophysical and biological properties of cooperative antisense oligonucleotides." Nucleic acids research 23.17 (1995): 3578-3584.
International Preliminary Report on Patentability issued for Application No. PCT/US2019/052957, dated Apr. 8, 2021.
Lebedev, A., "Heat-Activatable Primers for Hot-Start PCR: Oligonucleotide Synthesis and Basic PCR Setup," Current Protocols in Nucleic Acid Chemistry, Chapter 4, Unit 4.35, 2009, 17 pages.
Lebedev, Alexandre V., et al. "Hot Start PCR with heat-activatable primers: a novel approach for improved PCR performance." Nucleic acids research 36.20 (2008): e131-e131.
O'Meara, Deirdre, et al., "Cooperative Oligonucleotides Mediating Direct Capture of Hepatitis C Virus RNA from Serum," Journal of Clinical Microbiology, vol. 36, No. 9, Sep. 1998, pp. 2454-2459.
Piepenburg Melting Temp, Oligo Calc, accessed online Jan. 7, 2014.
Piepenburg et al., DNA detection Using Recombination Proteins, PLOS Biol. 2006, 4(7), e204, pp. 1115-1121.
Poritz, M.A., et al., "Getting Things Backwards to Prevent Primer Dimers," The Journal of Molecular Diagnostics, vol. 16, Issue 2, Mar. 2014, pp. 159-162.
Sambrook, J., et al., "Molecular Cloning: A Laboratory Manual: 2nd Edition," Cold Spring Harbor Laboratory Press, Cold Spring Harbor, New York, Chapters 5 and 6, 1989, 97 pages.
Zhou, Luming, et al. "Snapback primer genotyping with saturating DNA dye and melting analysis." Clinical chemistry 54.10 (2008): 1648-1656.
International Search Report and Written Opinion issued for Application No. No. PCT/US2013/050811, dated Nov. 26, 2013.
International Search Report and Written Opinion issued for Application No. PCT/US2022/31913, dated Sep. 9, 2022.
International Search Report and Written Opinion issued for Application No. PCT/US2023/65132, dated Sep. 5, 2023.
Supplementary Search report issued in European Application No. EP 13820614, dated Jan. 14, 2016.
Office Action Issued in Chinese Application No. 201380041220.2, dated May 5, 2016.
Wahl, Geoffrey M., Shelby L. Barger, and Alan R. Kimmel. "[43] Molecular hybridization of immobilized nucleic acids: Theoretical concepts and practical considerations." Methods in Enzymology. Vol. 152. Academic Press, 1987. 399- 407.
Kimmel, Alan R. "[54] Identification and characterization of specific clones: Strategy for confirming the validity of presumptive clones." Methods in Enzymology. Vol. 152. Academic Press, 1987. 507-511.
Eom, Soo Hyun, Jimin Wang, and Thomas A. Steitz. "Structure of Taq polymerase with DNA at the polymerase active site." Nature 382.6588 (1996): 278-281.
Braasch, Dwaine A., and David R. Corey. "Locked nucleic acid (LNA): fine-tuning the recognition of DNA and RNA." Chemistry & biology 8.1 (2001): 1-7.

(56) References Cited

OTHER PUBLICATIONS

Garbesi, Anna, et al. "L-DNAs as potenital antimessenger oligonucleotides: a reassessment." Nucleic acids research 21.18 (1993): 4159-4165.
Fujimori, Shizuyoshi, Koichi Shudo, and Yuichi Hashimoto. "Enantio-DNA recognizes complementary RNA but not complementary DNA." Journal of the American Chemical Society 112.20 (1990): 7436-7438.
Urata, Hidehito, et al. "Spectroscopic characterization of heterochiral DNAs." Nucleic Acids Symposium Series. No. 29. 1993.
Miller, Paul S. "A brief guide to nucleic acid chemistry." Bioconjugate Chemistry 1.3 (1990): 187-191.
Verma, Sandeep, and Fritz Eckstein. "Modified oligonucleotides: synthesis and strategy for users." Annual review of biochemistry 67.1 (1998): 99-134.
The Glen Report, 16(2):5 (2003).
Koshkin, Alexei A., et al. "LNA (Locked Nucleic Acids): Synthesis of the adenine, cytosine, guanine, 5-methylcytosine, thymine and uracil bicyclonucleoside monomers, oligomerisation, and unprecedented nucleic acid recognition." tetrahedron 54.14 (1998): 3607-3630.
Egholm, Michael, et al. "Peptide nucleic acids (PNA). Oligonucleotide analogs with an achiral peptide backbone." Journal of the American Chemical Society 114.5 (1992): 1895-1897.
Demidov, Vadim V., et al. "Kinetics and mechanism of the DNA double helix invasion by pseudocomplementary peptide nucleic acids." Proceedings of the National Academy of Sciences 99.9 (2002): 5953-5958.
Goodchild, John. "Conjugates of oligonucleotides and modified oligonucleotides: a review of their synthesis and properties." Bioconjugate Chemistry 1.3 (1990): 165-187.
Saiki, "Amplification of Genomic DNA" in PCR Protocols, Innis et al., Eds., Academic Press, San Diego, Calif. 1990, pp. 13-20. https://books.google.ro/books?hl=en&lr=&id=Z5jwZ2rbVe8C&oi=fnd&pg=PA13 &ots=ICITLIVTcC&sig=KMSs50MT5N8MCIE-JgASqYpgVe8&redir esc=y#v=onepage&q&f=false.
Wharam, Susan D., et al. "Specific detection of DNA and RNA targets using a novel isothermal nucleic acid amplification assay based on the formation of a three-way junction structure." Nucleic Acids Research 29.11 (2001): e54-e54.
Hafner, G. J., et al. "Isothermal amplification and multimerization of DNA by Bst DNA polymerase." Biotechniques 30.4 (2001): 852-867.
Office Action issued for Canadian Application No. 3,114,004, dated Jun. 3, 2024.
Office Action issued for Canadian Application No. 3,114,004, dated Jan. 23, 2024.

* cited by examiner

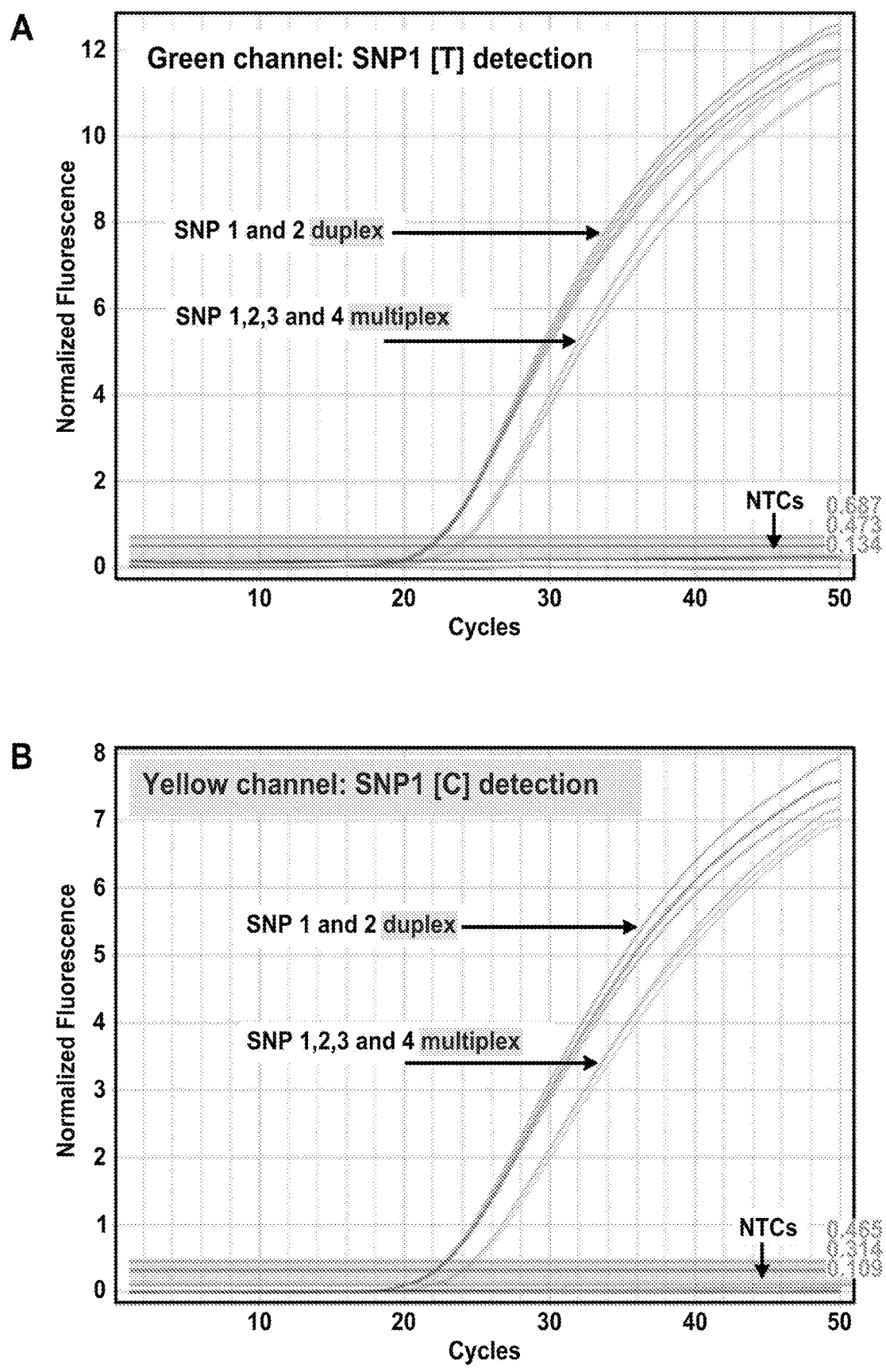
FIG. 4A-D

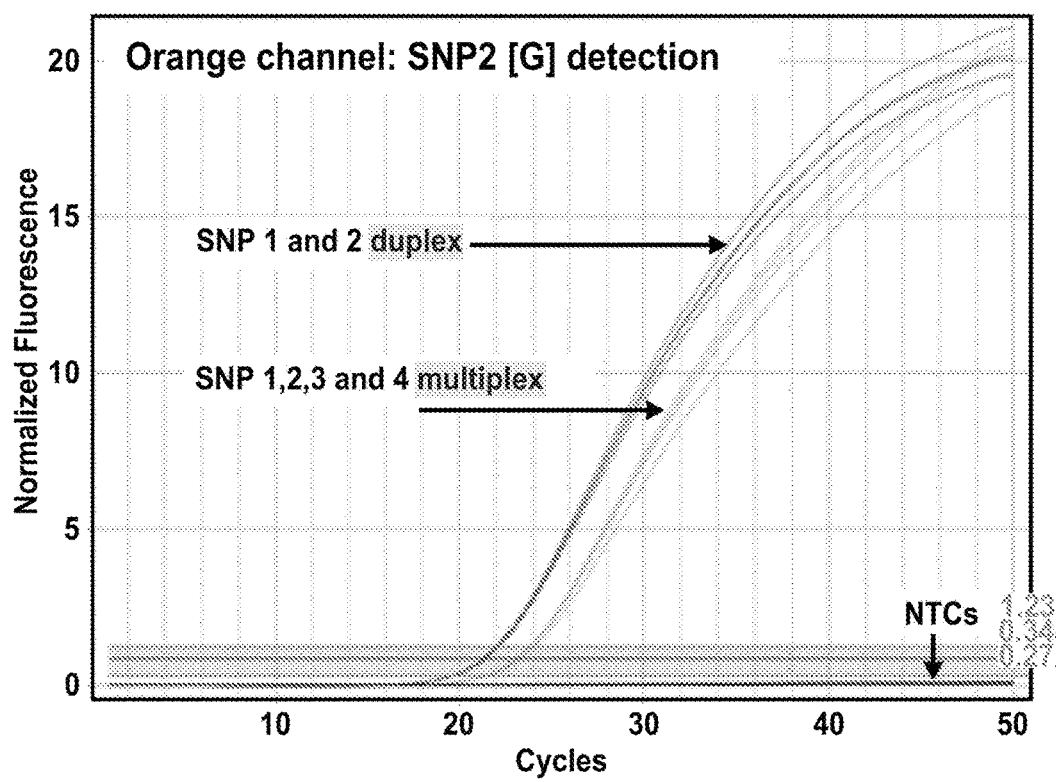
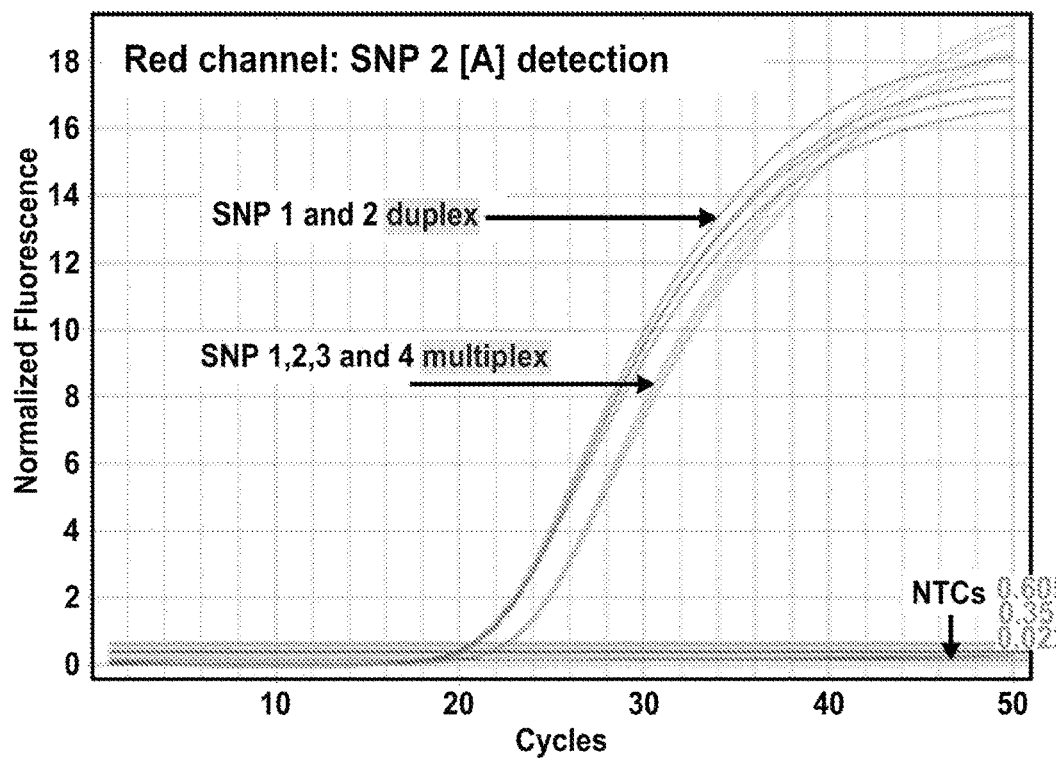
FIG. 4A-D CONT.

i)
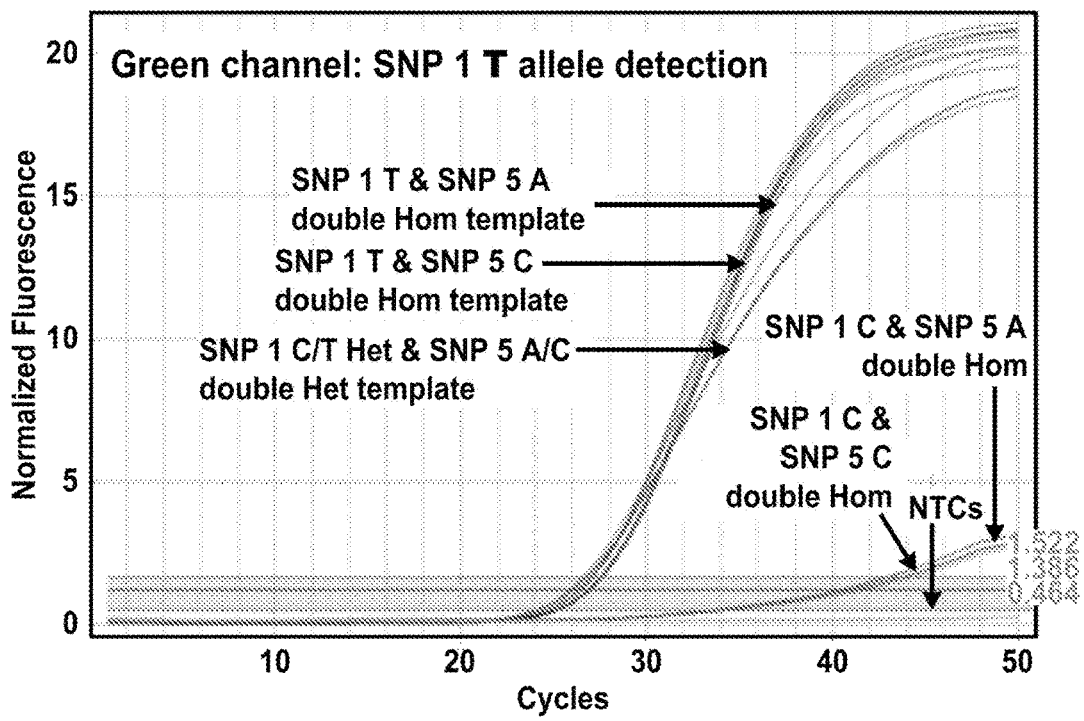
ii)
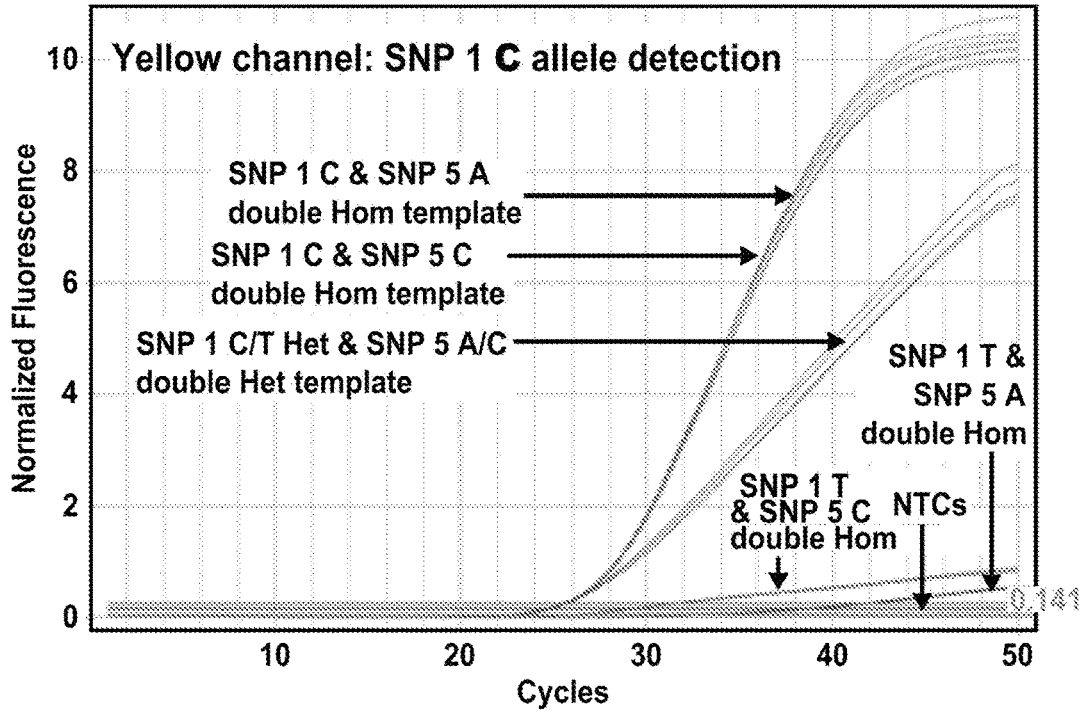
FIG. 5A CONT.

iii)
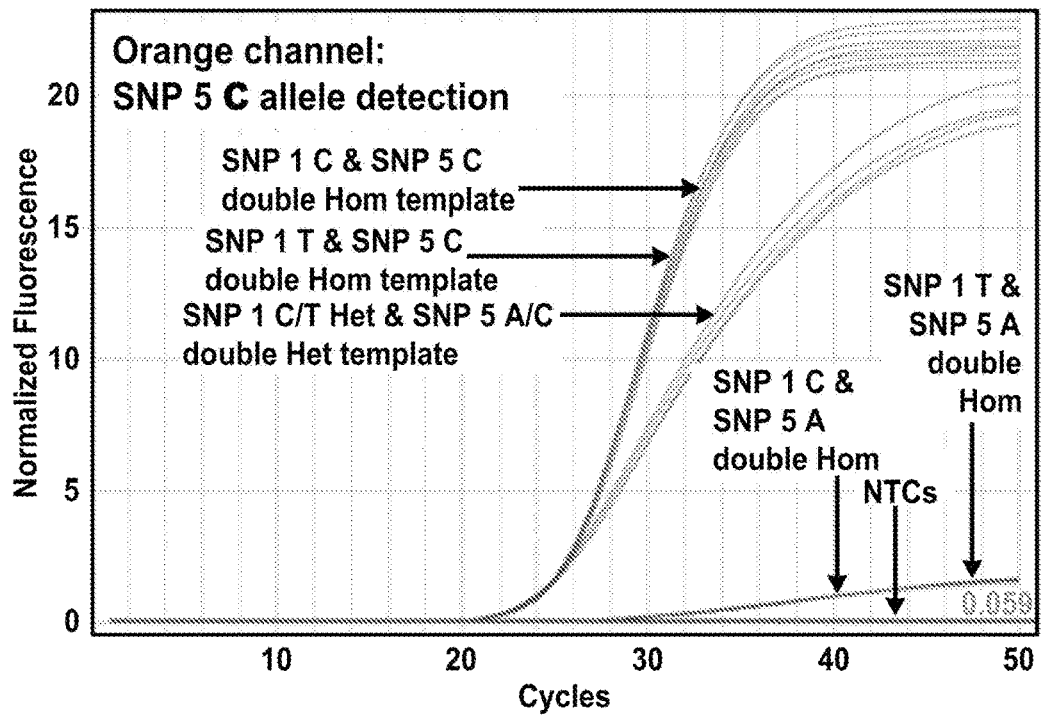
iv)
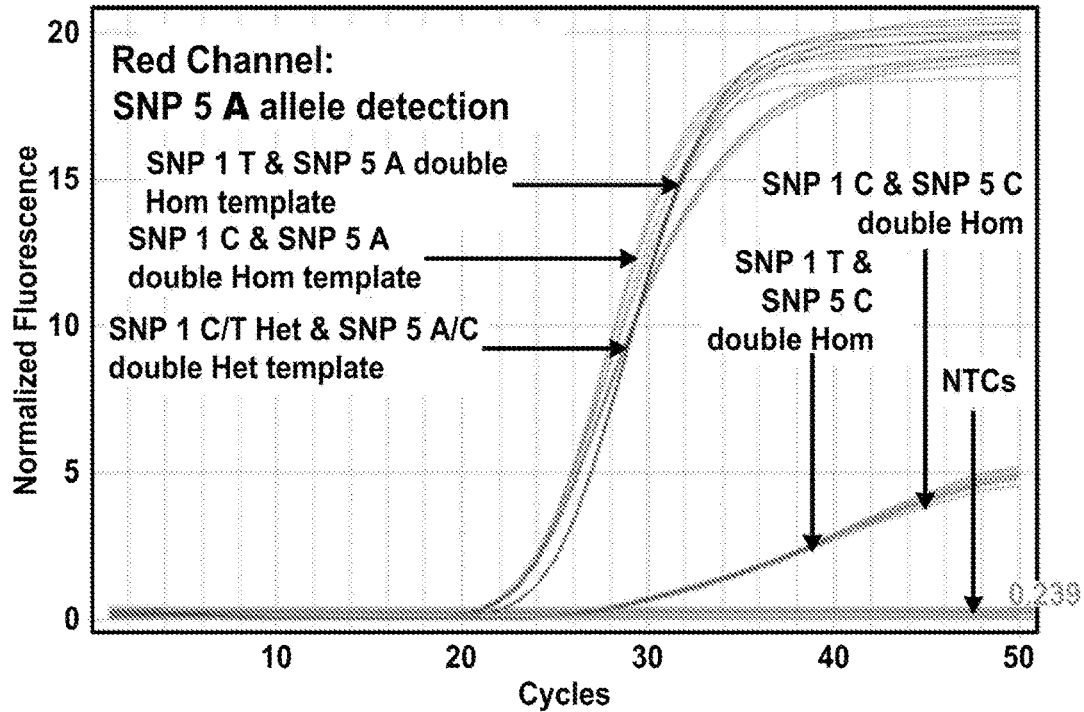
FIG. 5A CONT.

| Samples | |
|---|---|
| 1 | SNP 1T SNP 3 G |
| 2 | SNP 1T SNP 3 G |
| 3 | SNP 1T SNP 3 G |
| 4 | SNP 1T SNP 3 G |
| 5 | SNP 1T SNP 3 T |
| 6 | SNP 1T SNP 3 T |
| 7 | SNP 1T SNP 3 T |
| 8 | SNP 1T SNP 3 T |
| 9 | SNP 1C SNP 3 G |
| 10 | SNP 1C SNP 3 G |
| 11 | SNP 1C SNP 3 G |
| 12 | SNP 1C SNP 3 G |
| 13 | SNP 1C SNP 3 T |
| 14 | SNP 1C SNP 3 T |
| 15 | SNP 1C SNP 3 T |
| 16 | SNP 1C SNP 3 T |
| 17 | SNP 1C/T SNP 3 G/T |
| 18 | SNP 1C/T SNP 3 G/T |
| 19 | SNP 1C/T SNP 3 G/T |
| 20 | SNP 1C/T SNP 3 G/T |
| 21 | NTC |
| 22 | NTC |
| 23 | NTC |
| 24 | NTC |

FIG. 5B i)
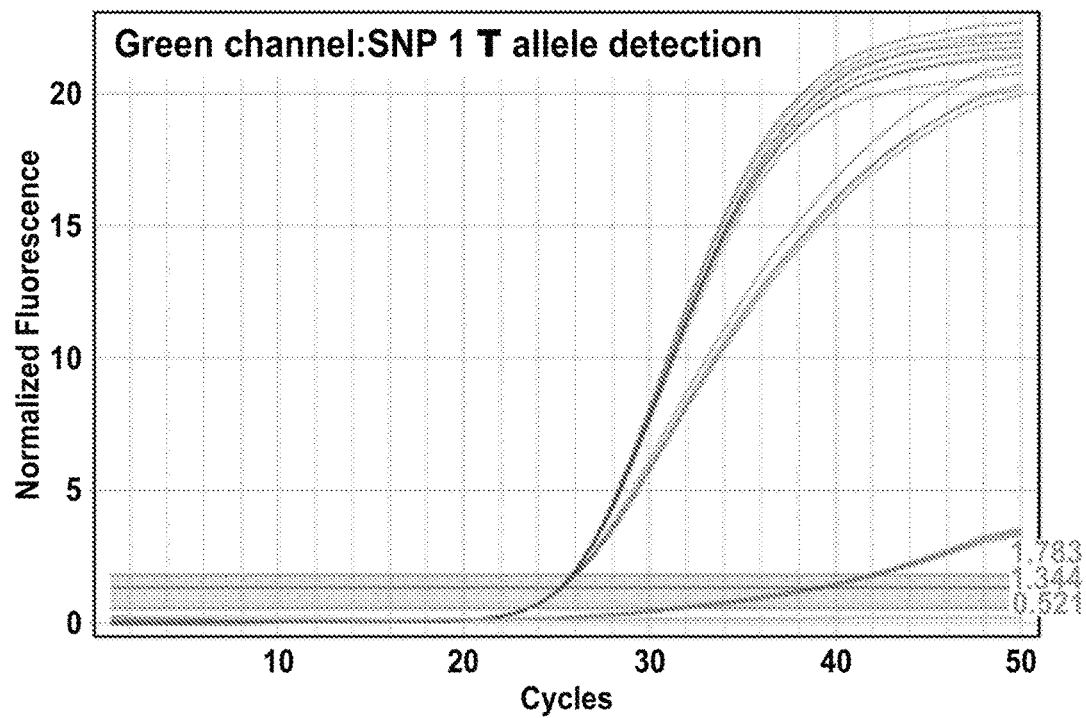
ii)
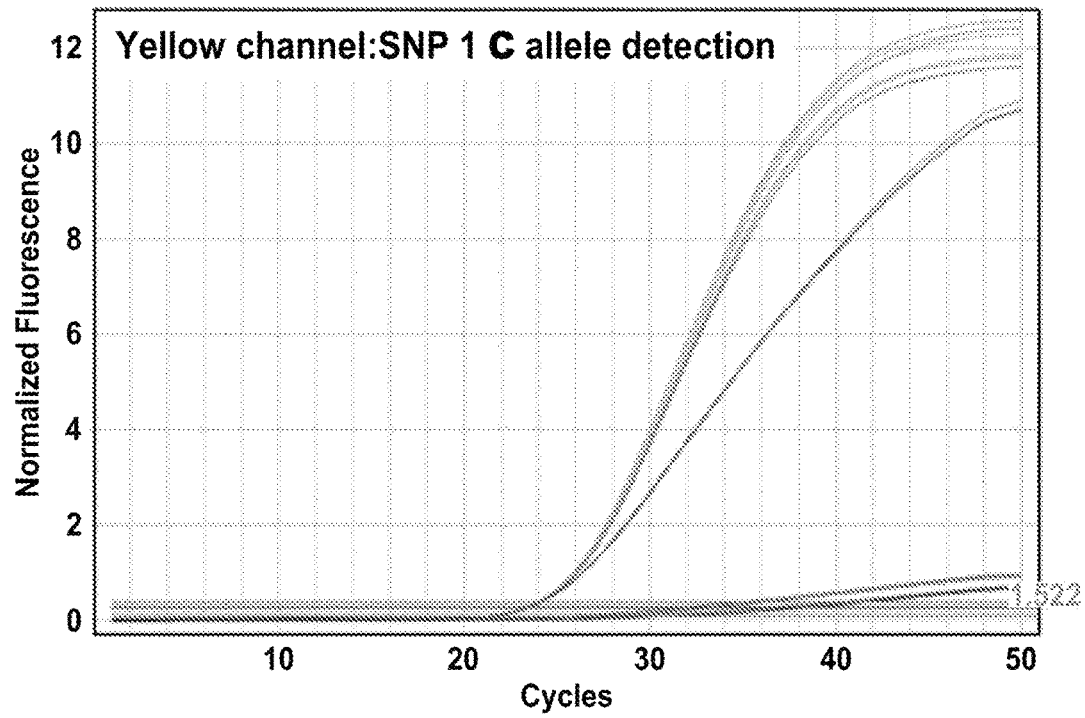
FIG. 5B CONT.

iii)
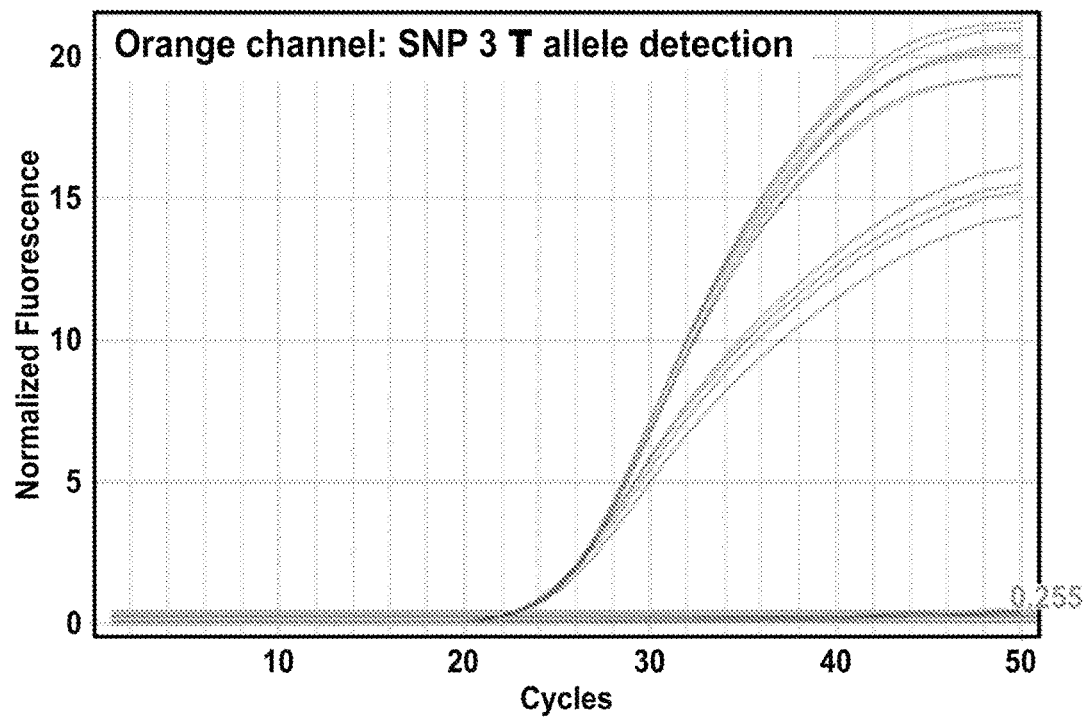
iv)
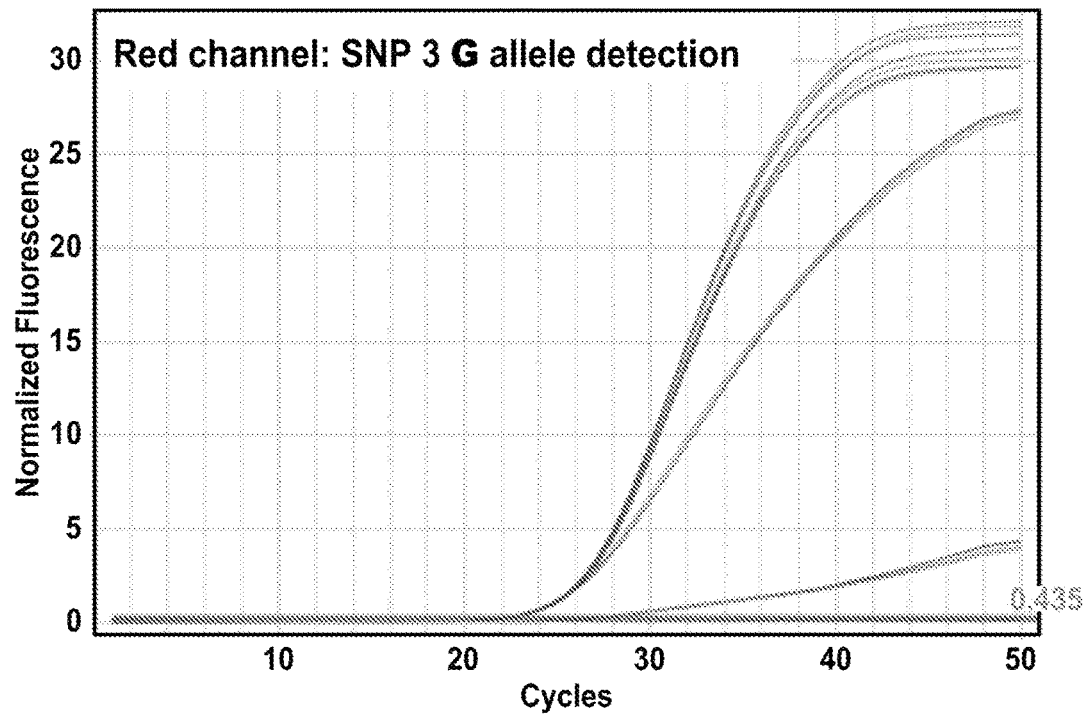
FIG. 5B CONT.

| Samples | |
|---|---|
| 1 | SNP 6C SNP 5A |
| 2 | SNP 6C SNP 5A |
| 3 | SNP 6C SNP 5A |
| 4 | SNP 6C SNP 5A |
| 5 | SNP 6C SNP 5C |
| 6 | SNP 6C SNP 5C |
| 7 | SNP 6C SNP 5C |
| 8 | SNP 6C SNP 5C |
| 9 | SNP 6G SNP 5A |
| 10 | SNP 6G SNP 5A |
| 11 | SNP 6G SNP 5A |
| 12 | SNP 6G SNP 5A |
| 13 | SNP 6G SNP 5C |
| 14 | SNP 6G SNP 5C |
| 15 | SNP 6G SNP 5C |
| 16 | SNP 6G SNP 5C |
| 17 | SNP 6C/G SNP 5A/C |
| 18 | SNP 6C/G SNP 5A/C |
| 19 | SNP 6C/G SNP 5A/C |
| 20 | SNP 6C/G SNP 5A/C |
| 21 | NTC |
| 22 | NTC |
| 23 | NTC |
| 24 | NTC |

FIG. 5C i)
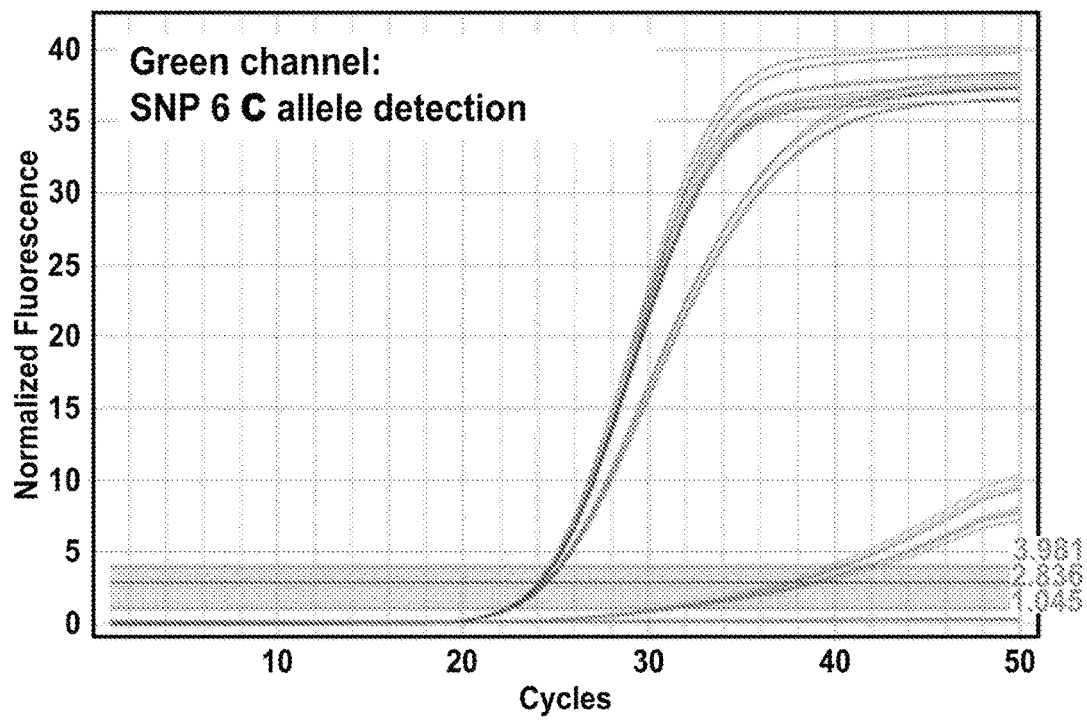
ii)
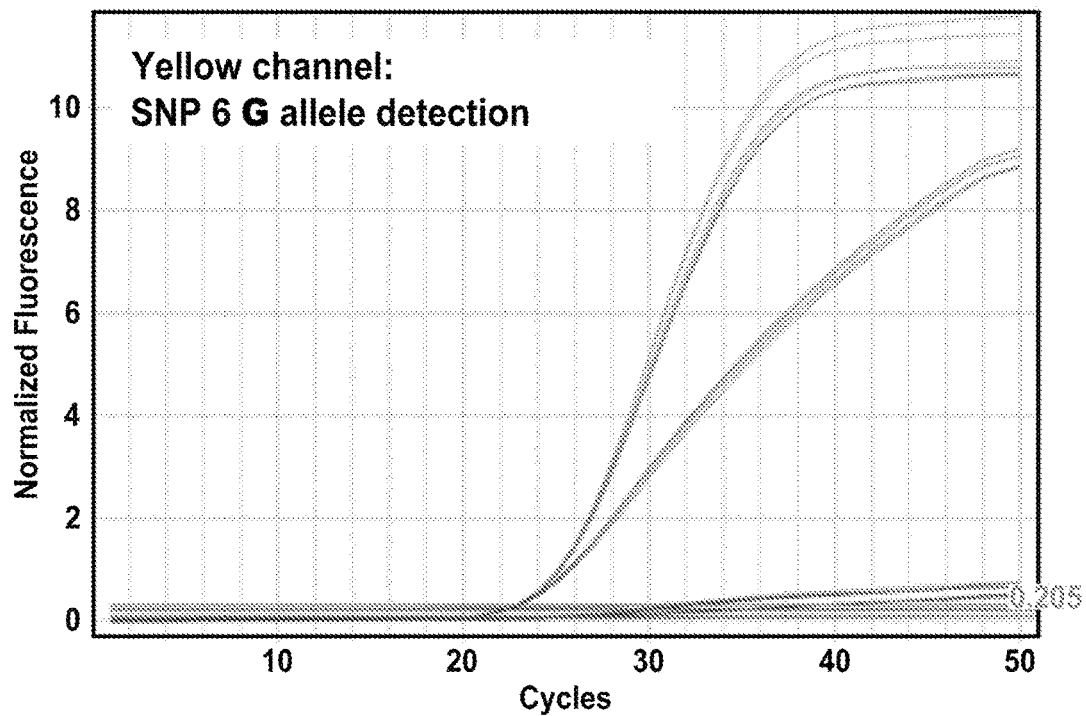
FIG. 5C CONT.

iii)
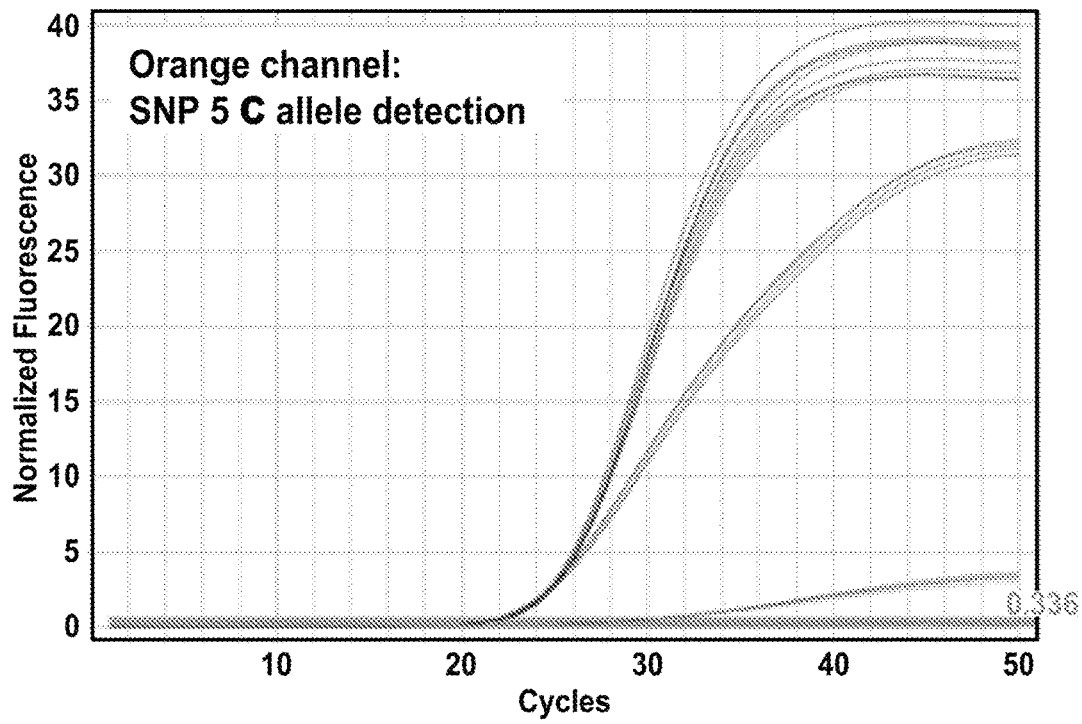
iv)
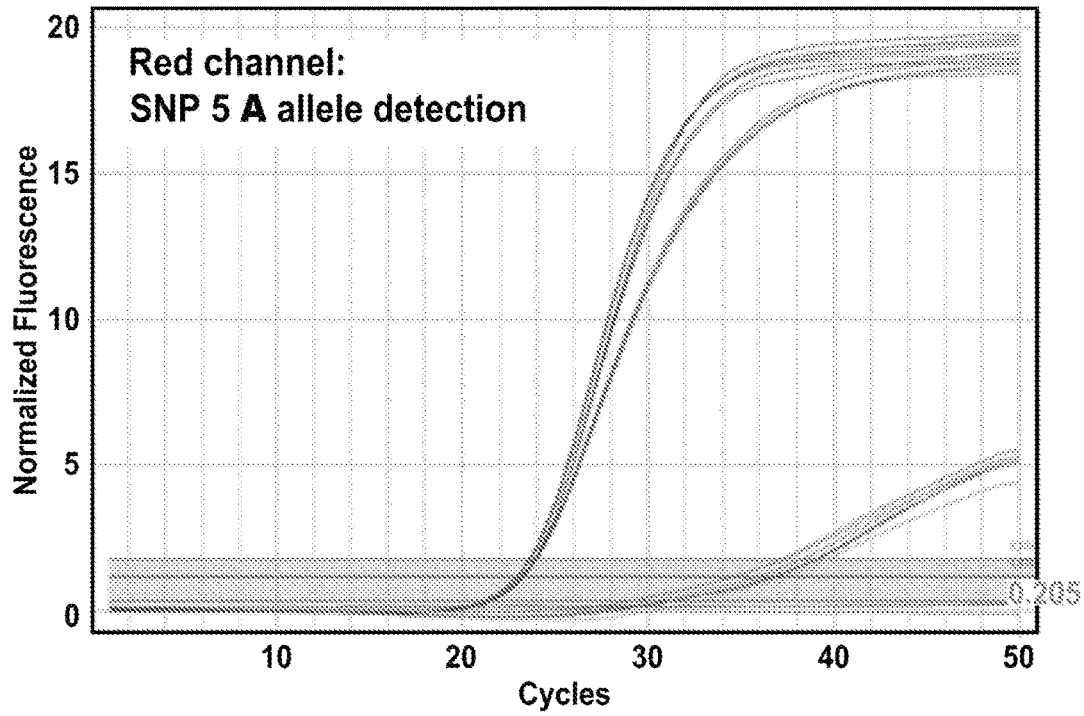
FIG. 5C CONT.

Collection of Labeled CoPrimers for MIX & MATCH Study:

| SNP ID \ Channel | FAM<br>GREEN | CAL Fluor Orange 560<br>YELLOW | Quasar 670<br>RED | CAL Fluor RED 610<br>ORANGE |
|---|---|---|---|---|
| SNP 1 T/C | SNP 1 T | SNP 1 C | SNP 1 T | SNP 1 C |
| SNP 2 A/C | SNP 2 A | SNP 2 G | SNP 2 A | SNP 2 G |
| SNP 4 A/G | SNP 4 A | SNP 4 G | | |
| SNP 3 G/T | | | SNP 3 G | SNP 3 T |
| SNP 5 A/C | | | SNP 5 A | SNP 5 C |
| SNP 6 C/G | SNP 6 C | SNP 6 G | | |

FIG. 5D

SNP under the CAPTURE

| OligoName | Gap length [bp] | Ct for WT template [cycles] | Ct for MUT template [cycles] | dCt (difference between WT and MUT Ct values) | AVERAGE dCt [cycles] | SD |
|---|---|---|---|---|---|---|
| SNP2.F9 | 1 | 28 | 40 | 12 | 8 | 4.8 |
| SNP1.W.F3 | 2 | 26 | 40 | 14 | | |
| SNP1.W.F10 | 2 | 23 | 24 | 1 | | |
| SNP3.F11 | 2 | 39 | >50 | 11 | | |
| SNP3.F12 | 2 | 25 | 30 | 5 | | |
| SNP3.F13 | 2 | 30 | 38 | 8 | | |
| SNP1.W.F2 | 3 | 28 | 41 | 13 | | |
| SNP1.W.F1 | 4 | 23 | 26 | 3 | | |
| SNP1.W.F9 | 5 | 23 | 27 | 4 | | |

Note: dCt values too inconsistent, sometimes very low. The matched Ct** values sometimes too high.

SNP under the PRIMING; -1*

| OligoName | Gap length [bp] | Ct for WT template [cycles] | Ct for MUT template [cycles] | dCt (difference between WT and MUT Ct values) | AVERAGE dCt [cycles] | SD |
|---|---|---|---|---|---|---|
| SNP1.W.F11 | 2 | 27 | 42 | 15 | 12 | 2.8 |
| SNP3.F6 | 3 | 25 | 33 | 8 | | |
| SNP3.F5 | 3 | 25 | 33 | 8 | | |
| SNP4.F3 | 4 | 24 | 34 | 10 | | |
| SNP1.W.F4 | 5 | 24 | 38 | 14 | | |
| SNP1.W.F5 | 5 | 27 | 40 | 13 | | |
| SNP4.F4 | 7 | 24 | 36 | 13 | | |

Note: dCt values great and consistent.

FIG. 14

SNP under the PRIMING: -2

| OligoName | Gap length [bp] | Ct for WT template [cycles] | Ct for MUT template [cycles] | dCt (difference between WT and MUT Ct values) | Note: Good matched Ct values, good dCt values consistency. |
|---|---|---|---|---|---|
| SNP2.F1 | 1 | 26 | 37 | 12 | |
| SNP1.W.F12 | 2 | 27 | 42 | 15 | |
| SNP2.F3 | 2 | 25 | 32 | 7 | |
| SNP3.F1 | 2 | 25 | 37 | 12 | |
| SNP3.F2 | 2 | 24 | 37 | 13 | |
| SNP4.F1 | 3 | 24 | 32 | 24 | |
| SNP1.W.F7 | 4 | 29 | 41 | 12 | |
| SNP1.W.F6 | 5 | 24 | 36 | 12 | |
| SNP1.W.F8 | 5 | 26 | 40 | 14 | |
| SNP4.F2 | 6 | 24 | 35 | 11 | |

| AVERAGE dCt [cycles] | SD |
|---|---|
| 13 | 24.3 |

SNP under the PRIMING: -3

| OligoName | Gap length [bp] | Ct for WT template [cycles] | Ct for MUT template [cycles] | dCt (difference between WT and MUT Ct values) | Note: dCt are variable, in about half the cases too low. |
|---|---|---|---|---|---|
| SNP2.F2 | 0 | 25 | 36 | 11 | |
| SNP2.F4 | 1 | 25 | 30 | 4 | |
| SNP3.F3 | 1 | 25 | 35 | 10 | |
| SNP3.F4 | 1 | 25 | 40 | 15 | |
| SNP1.W.F13 | 4 | 24 | 30 | 6 | |
| SNP1.W.F14 | 5 | 24 | 31 | 7 | |

| AVERAGE dCt [cycles] | SD |
|---|---|
| 9 | 3.9 |

FIG. 14 CONT.

| SNP under the PRIMING; -1, -2 | | | | |
|---|---|---|---|---|
| OligoName | Gap length [bp] | Ct for WT template [cycles] | Ct for MUT template [cycles] | dCt (difference between WT and MUT Ct values) |
| SNP1.W.F15 | 2 | 46 | >55 | >9 |
| SNP1.W.F16 | 5 | 46 | >55 | >9 |
| SNP1.W.F17 | 5 | 42 | >55 | >8 |

Note: Matched Cts too high.

| SNP under the PRIMING; -2, -3 | | | | |
|---|---|---|---|---|
| OligoName | Gap length [bp] | Ct for WT template [cycles] | Ct for MUT template [cycles] | dCt (difference between WT and MUT Ct values) |
| SNP2.F5 | 1 | 27 | 42 | 14 |
| SNP2.F6 | 2 | 30 | 38 | 8 |
| SNP4.F5 | 3 | 39 | >50 | >11 |
| SNP1.W.F19 | 4 | 45 | >50 | >5 |
| SNP1.W.F18 | 5 | 38 | >50 | >12 |
| SNP1.W.F20 | 5 | 45 | >50 | >5 |
| SNP1.W.F21 | 5 | 36 | >50 | >14 |
| SNP4.F6 | 6 | 40 | >50 | >10 |

Note: Matched Cts are, in most cases, too high. The dCt values are inconsistent, but sometimes very good.

FIG. 14 CONT.

| SNP under the PRIMING; -1, or -2, or -2/-3, or -3/-4 with additional 3 or 4 mismatches | | | | | |
|---|---|---|---|---|---|
| OligoName | Gap length [bp] | Ct for WT template [cycles] | Ct for MUT template [cycles] | dCt (difference between WT and MUT Ct values) | Note: Matched Cts are, in most cases, way too high. With some designs though, the dCt is good. |
| SNP2.F7 | 1 | 28 | 38 | 10 | |
| SNP1.W.F24 | 2 | >50 | 34 | >16 | |
| SNP1.W.F25 | 2 | 51 | 32 | 19 | |
| SNP3.F9 | 2 | 40 | 25 | 14 | |
| SNP3.F10 | 2 | 42 | 25 | 17 | |
| SNP2.F8 | 2 | 26 | 35 | 9 | |
| SNP4.F7 | 3 | 27 | 36 | 9 | |
| SNP1.W.F27 | 4 | 43 | 30 | 13 | |
| SNP1.W.F28 | 4 | >60 | 48 | >12 | |
| SNP1.W.F29 | 5 | >60 | 42 | >18 | |
| SNP1.W.F30 | 5 | Random Cts | | N/A | |
| SNP4.F8 | 6 | 28 | 38 | 10 | |

*) Position of the variant-induced mismatch is indicated by a negative number. Ultimate base, (-1); penultimate base, (-2); antepenultimate base, (-3). Both penultimate and antepenultimate bases, (-2/-3) etc..
**) Ct value for a reaction involving CoPrimer matching its template

FIG. 14 CONT.

| SNP ID | Alleles | Primer ID | Priming Tm [°C] | Capture Tm [°C] | dCt [cycles] |
|---|---|---|---|---|---|
| 1 | C | F12 | 49.9 | 53.4 | 17.1 |
|   | T | F12 | 52.4 |  |  |
|   |   | R1 | 54.5 | 56.1 |  |
| 2 | A | F1 | 51.5 | 53.8 | 15.0 |
|   | G | F1 | 55.3 |  |  |
|   |   | R6 | 38.5 | 59.6 |  |
| 3 | G | F2 | 50.0 | 53.7 | 17.1 |
|   | T | F2 | 45.6 |  |  |
|   |   | R3 | 50.0 | 52.5 |  |
| 4 | A | F2 | 45.4 | 52.5 | 13.2 |
|   | G | F2 | 48.9 |  |  |
|   |   | R4 | 52.7 | 53.7 |  |
| 5 | C | F1 | 50.2 | 52.8 | 13.6 |
|   | A | F1 | 47.6 |  |  |
|   |   | R1 | 41.8 | 57.47 |  |
| 6 | C | F1 | 52.2 | 56 | 17.5 |
|   | G | F1 | 51.9 |  |  |
|   |   | R1 | 52.3 | 53.2 |  |
| 7 | A | F2 | 51.8 | 52.1 | 14.0 |
|   | G | F2 | 54.6 |  |  |
|   |   | R1 | 50.1 | 53.5 |  |
| 8 | A | F1 | 51.6 | 55.1 | 16.5 |
|   | T | F1 | 52.4 |  |  |
|   |   | R3 | 50.2 | 53.8 |  |
| 9 | T | F1 | 51.0 | 56.9 | 15.5 |
|   | delT | F6 | 50.3 |  |  |
|   |   | R1 |  |  |  |

FIG. 15

ALLELE-SPECIFIC DESIGN OF COOPERATIVE PRIMERS FOR IMPROVED NUCLEIC ACID VARIANT GENOTYPING

CROSS REFERENCE TO RELATED APPLICATIONS

This application is a United States National Phase Patent Application of International Patent Application Number PCT/US2019/052957, filed on Sep. 25, 2019, which claims benefit of U.S. Provisional Application No. 62/736,094, filed Sep. 25, 2018, incorporated herein by reference in its entirety.

BACKGROUND

"Cooperative Primers," as they are known in the art, drastically reduce primer-dimer formation and propagation. However, application for cooperative primers for differentiation between closely related strains (especially those with only a difference between one or a few nucleotides, such as SNPs) has had little or no success. Detection limitations only allowed differentiation in narrow applications, notably those where allele concentration was known prior to testing. What is needed in the art is the ability to distinguish between nucleic acids, even those with a single nucleotide difference, such as a SNP.

SUMMARY

Disclosed herein is a method of synthesizing a target nucleic acid preferentially relative to a nucleic acid with one or more nucleotides that differ from the target nucleic acid, the method comprising: a) exposing a cooperative nucleic acid molecule to a solution suspected of comprising a target nucleic acid and also potentially comprising a nucleic acid with one or more nucleotides that differ from the target nucleic acid (differing nucleic acid), wherein the cooperative nucleic acid molecule comprises, from 3' to 5': i) a first nucleic acid sequence, wherein the first nucleic acid sequence is complementary to a first region of a target nucleic acid, and further wherein a penultimate nucleotide of the 3' end of the first nucleic acid sequence is complementary to the target nucleic acid, but is not complementary to the differing nucleic acid, and yet further wherein the first nucleic acid is extendable on the 3' end; ii) a second nucleic acid sequence, wherein the second nucleic acid sequence is complementary to a second region of the target nucleic acid, wherein the complementarity between the second nucleic acid sequence and the target nucleic acid starts within one nucleotide or less of the first region of the target nucleic acid, such that it hybridizes to the target nucleic acid downstream from the 3' end of the first nucleic acid sequence, or overlaps on the 5' end with the 3' end of the first nucleic acid sequence; iii) a linker connecting said first and second nucleic acid sequences in a manner that allows both the said first and second nucleic acid sequences to hybridize to the target nucleic acid at the same time; b) providing conditions appropriate for nucleic acid synthesis wherein the polymerase extends from the 3' end of the first nucleic acid sequence through the second nucleic acid sequence, thereby synthesizing the target nucleic acid preferentially to the differing nucleic acid if it is present in the solution.

BRIEF DESCRIPTION OF THE DRAWINGS

The accompanying figures, which are incorporated in and constitute a part of this specification, illustrate several aspects and together with the description serve to explain the principles of the invention.

FIG. 2B is showing the mismatch under the Priming, at the ultimate position. FIG. 2C shows mismatch under the Priming, at a penultimate position, with extra intentional mismatches under the 5' portion of the Priming.

FIG. 4A-D shows duplex vs. multiplex efficiency studies.

FIG. 5A-D shows the results of a Mix and Match Study, which allowed genotyping results to be obtained for 6 SNPs, mixed in all possible combinations (fluorophore-permitting)

FIG. 14 shows mismatch at various positions in cooperative primer nucleic acids.

FIG. 15 shows that when variant-induced mismatch was placed under the capture sequence, the dCt values (demonstrating the differentiation power of allele-specific CoPrimers) were very variable, averaging at 8 cycles with standard deviation of 4.8 cycles.

Figure 1:
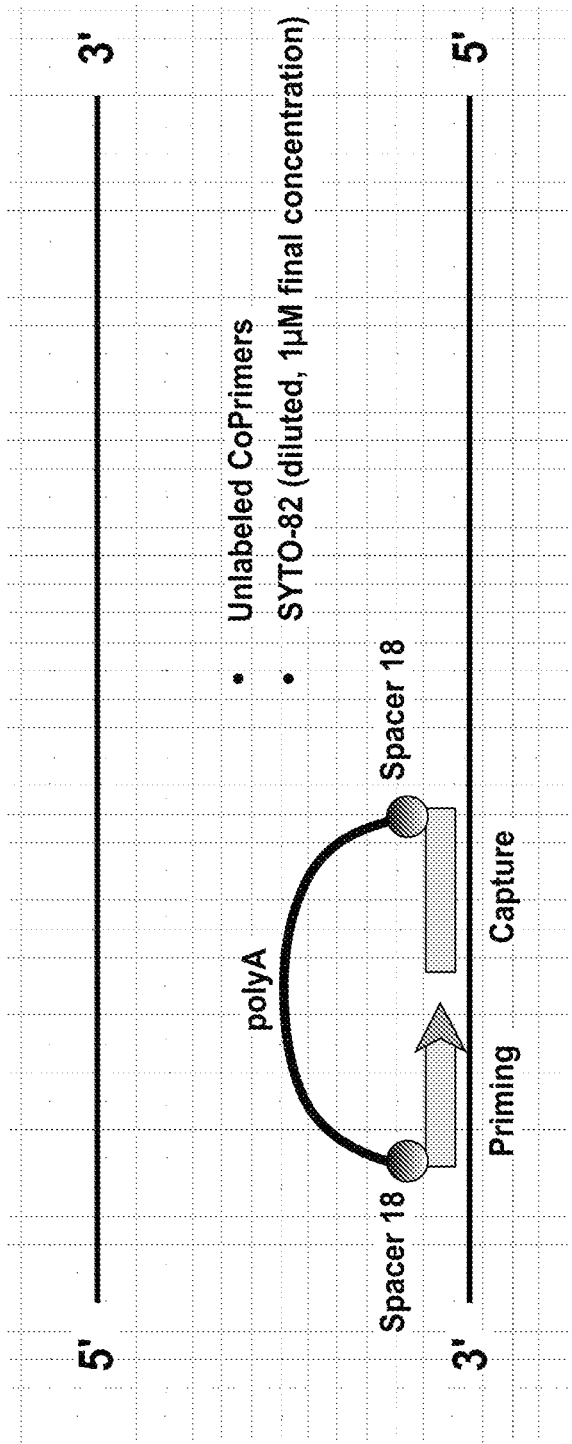
FIG. 1 shows a general structure of the co-primer.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The disclosed method makes use of certain materials and procedures which allow amplification of nucleic acid sequences and whole genomes or other highly complex nucleic acid samples. These materials and procedures are described in detail below.

Definitions

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used herein, "nucleic acid sequence" refers to the order or sequence of nucleotides along a strand of nucleic acids. In some cases, the order of these nucleotides may determine the order of the amino acids along a corresponding polypeptide chain. The nucleic acid sequence thus codes for the amino acid sequence. The nucleic acid sequence may be single-stranded or double-stranded, as specified, or contain portions of both double-stranded and single-stranded sequences. The nucleic acid sequence may be composed of DNA, both genomic and cDNA, RNA, or a hybrid, where the sequence comprises any combination of deoxyribo- and ribo-nucleotides, and any combination of bases, including uracil (U), adenine (A), thymine (T), cytosine (C), guanine (G), inosine, xathanine hypoxathanine, isocytosine, isoguanine, etc. It may include modified bases, including locked nucleic acids, peptide nucleic acids and others known to those skilled in the art.

An "oligonucleotide" is a polymer comprising two or more nucleotides. The polymer can additionally comprise non-nucleotide elements such as labels, quenchers, blocking groups, or the like. The nucleotides of the oligonucleotide can be natural or non-natural and can be unsubstituted, unmodified, substituted or modified. The nucleotides can be linked by phosphodiester bonds, or by phosphorothioate linkages, methylphosphonate linkages, boranophosphate linkages, or the like.

A "peptide nucleic acid" (PNA) is a polymer comprising two or more peptide nucleic acid monomers. The polymer can additionally comprise elements such as labels, quenchers, blocking groups, or the like. The monomers of the PNA can be unsubstituted, unmodified, substituted or modified.

By "cooperative nucleic acid" is meant a) a first nucleic acid sequence, wherein the first nucleic acid sequence is complementary to a first region of a target nucleic acid, and further wherein a penultimate nucleotide of the 3' end of the first nucleic acid sequence is complementary to the target nucleic acid, and yet further wherein the first nucleic acid is extendable on the 3' end and extension can proceed from the ultimate nucleotide, past the penultimate nucleotide; and b) a second nucleic acid sequence, wherein the second nucleic acid sequence is complementary to a second region of the target nucleic acid, wherein the complementarity between the second nucleic acid sequence and the target nucleic acid starts within two nucleotides or less of the first region of the target nucleic acid, such that it hybridizes to the target nucleic acid downstream from the 3' end of the first nucleic acid sequence. The first and second nucleic acid sequences can be separated by a linker, for example.

A "primer" is a nucleic acid that contains a sequence complementary to a region of a template nucleic acid strand and that primes the synthesis of a strand complementary to the template (or a portion thereof). Primers are typically, but need not be, relatively short, chemically synthesized oligonucleotides (typically, deoxyribonucleotides). In an amplification, e.g., a PCR amplification, a pair of primers typically define the 5' ends of the two complementary strands of the nucleic acid target that is amplified. By "normal primer" is meant a primer which does not have a capture sequence, or second nucleic acid sequence, attached to it via a linker.

By "capture sequence," which is also referred to herein as a "second nucleic acid sequence" is meant a sequence which hybridizes to the target nucleic acid and allows the first nucleic acid sequence, or primer sequence, to be in close proximity to the target region of the target nucleic acid.

"Downstream" is relative to the action of the polymerase during nucleic acid synthesis or extension. For example, when the Taq polymerase extends a primer, it adds bases to the 3' end of the primer and will move towards a sequence that is "downstream from the 3' end of the primer."

A "target region" is a region of a target nucleic acid that is to be amplified, detected or both.

The "Tm" (melting temperature) of a nucleic acid duplex under specified conditions is the temperature at which half of the nucleic acid sequences are disassociated and half are associated. (Tm calculations used as suggested by John SantaLucia in "The Thermodynamics of DNA Structural Motifs"). As used herein, "isolated Tm" refers to the individual melting temperature of either the first or second nucleic acid sequence in the cooperative nucleic acid when not in the cooperative pair. "Effective Tm" refers to the resulting melting temperature of either the first or second nucleic acid when linked together.

The term "linker" means the composition joining the first and second nucleic acids to each other. The linker comprises at least one non-extendable moiety, but may also comprise extendable nucleic acids, and can be any length. The linker may be connected to the 3' end, the 5' end, or can be connected one or more bases from the end ("the middle") of both the first and second nucleic acid sequences. The connection can be covalent, hydrogen bonding, ionic interactions, hydrophobic interactions, and the like. The term "non-extendable" has reference to the inability of the native Taq polymerase to recognize a moiety and thereby continue nucleic acid synthesis. A variety of natural and modified nucleic acid bases are recognized by the polymerase and are "extendable." Examples of non-extendable moieties include among others, fluorophores, quenchers, polyethylene glycol, polypropylene glycol, polyethylene, polypropylene, polyamides, polyesters and others known to those skilled in the art. In some cases, even a nucleic acid base with reverse orientation (e.g. 5' ACGT 3' 3'A 5' 5' AAGT 3') or otherwise rendered such that the Taq polymerase could not extend through it could be considered "non-extendable."

The term "non-nucleic acid linker" as used herein refers to a reactive chemical group that is capable of covalently attaching a first nucleic acid to a second nucleic acid, or more specifically, the primer to the capture sequence. Suitable flexible linkers are typically linear molecules in a chain of at least one or two atoms, more typically an organic polymer chain of 1 to 12 carbon atoms (and/or other backbone atoms) in length. Exemplary flexible linkers include polyethylene glycol, polypropylene glycol, polyethylene, polypropylene, polyamides, polyesters and the like.

As used herein, "complementary" or "complementarity" refers to the ability of a nucleotide in a polynucleotide molecule to form a base pair with another nucleotide in a second polynucleotide molecule. For example, the sequence 5'-A-C-T-3' is complementary to the sequence 3'-T-G-A-5'. Complementarity may be partial, in which only some of the nucleotides match according to base pairing, or complete, where all the nucleotides match according to base pairing. For purposes of the present invention "substantially complementary" refers to 90% or greater identity over the length of the target base pair region. The complementarity can also be 50, 60, 70, 75, 80, 85, 90, 91, 92, 93, 94, 95, 96, 97, 98, 99, or 100% complementary, or any amount below or in between these amounts.

As used herein, "amplify, amplifying, amplifies, amplified, amplification" refers to the creation of one or more identical or complementary copies of the target DNA. The copies may be single stranded or double stranded. Amplification can be part of a number of processes such as extension of a primer, reverse transcription, polymerase chain reaction, nucleic acid sequencing, rolling circle amplification and the like.

As used herein, "purified" refers to a polynucleotide, for example a target nucleic acid sequence, that has been separated from cellular debris, for example, high molecular weight DNA, RNA and protein. This would include an isolated RNA sample that would be separated from cellular debris, including DNA. It can also mean non-native, or non-naturally occurring nucleic acid.

As used herein, "protein," "peptide," and "polypeptide" are used interchangeably to denote an amino acid polymer or a set of two or more interacting or bound amino acid polymers.

As used herein, "stringency" refers to the conditions, i.e., temperature, ionic strength, solvents, and the like, under which hybridization between polynucleotides occurs. Hybridization being the process that occurs between the primer and template DNA during the annealing step of the amplification process.

As used herein, the term "differing nucleic acid" means that the nucleic acid differs by one or more nucleotides from the target nucleic acid. For example, a single nucleotide polymorphism (SNP) can have two different nucleotides (A, G, C, or T) at the same position in the nucleic acid molecule. The differing nucleic acid can also differ by more than one position, such that 2, 3, 4, 5, 6, 7, 8, 9, 10, or more differences exist between the differing nucleic acid and the target nucleic acid. These differences can include additions, deletions, inversions, or SNPs.

As used herein, the term "overlapping nucleotides" or "negative gap" is meant that the second region of complementarity between the second nucleic acid sequence and the target nucleic acid overlaps with the first region of complementarity of the target nucleic acid and the first nucleic acid sequence, such that the first and second regions overlap by one or more nucleotides. This is known as a "negative gap." For example, in the case of a −1 gap (a negative gap of one nucleotide, or put another way, one overlapping nucleotide), the 3' nucleotide of the first nucleic acid sequence and the 5' base of the second nucleic acid are complementary to the same nucleotide on the target nucleic acid. Likewise, with a −2 gap (a gap of two nucleotides, or put another way, two overlapping nucleotides), the 5' base of the first nucleic acid sequence is complementary to the differing strand while the penultimate 3' nucleotide of the second nucleic acid sequence is complementary to the target nucleic acid. In the case of a short gap, lack of perfect flexibility in the template leads to competition between the polymerase and the capture for space. Also, the polymerase cannot begin extending without immediate resistance from the capture sequence being bound.

A variety of additional terms are defined or otherwise characterized herein.

Materials and Methods

Disclosed herein is a method of discriminating between a target nucleic acid and a nucleic acid with one or more nucleotides that differ from the target nucleic acid, the method comprising: a) exposing a cooperative nucleic acid molecule to a solution comprising a target nucleic acid and also potentially comprising a nucleic acid with one or more nucleotides that differ from the target nucleic acid (differing nucleic acid), wherein the cooperative nucleic acid molecule comprises, from 3' to 5': i) a first nucleic acid sequence, wherein the first nucleic acid sequence is complementary to a first region of a target nucleic acid, and further wherein a penultimate nucleotide of the 3' end of the first nucleic acid sequence is complementary to the target nucleic acid, but is not complementary to the differing nucleic acid, and yet further wherein the first nucleic acid is extendable on the 3' end and extension can proceed from the ultimate nucleotide, past the penultimate nucleotide; ii) a second nucleic acid sequence, wherein the second nucleic acid sequence is complementary to a second region of the target nucleic acid, wherein the complementarity between the second nucleic acid sequence and the target nucleic acid is within one nucleotide or less of the first region of the target nucleic acid, such that it hybridizes to the target nucleic acid downstream from the 3' end of the first nucleic acid sequence, or overlaps at the 5' end of the first nucleic acid sequence; iii) a linker connecting said first and second nucleic acid sequences in a manner that allows both the said first and second nucleic acid sequences to hybridize to the target nucleic acid at the same time; b) providing conditions appropriate for nucleic acid synthesis, thereby synthesizing the target nucleic acid and not synthesizing the differing nucleic acid if it is present in the solution.

Without being limited to theory, there are several factors in differentiation of nucleic acids with one or more mismatches, insertions, deletions, and/or other modifications using co-primers which each have impact on SNP differentiation individually and in combination. These include, but are not limited to 1) the placement of the SNP or other mismatch on the first or priming sequence in the co-primer; 2) the gap size or number of nucleic acids between the 3' end of the extendable first sequence and the 5' end of the second sequence; 3) the presence of competing co-primers for the other allele; 4) the melting temperature (Tm) of the first and/or second sequence relative to the reaction temperature; 5) the addition of other mismatches intentionally placed in the first and/or second sequence; and 6) the type of master mix used.

For example, if the nucleic acid bases in the first sequence of the co-primer are numbered from the 3' end: 1, 2, 3, etc., then the SNP or other mismatch can be located under the 3' end of the first sequence also called base 1 or the first base. In another embodiment, the SNP or other mutation could be located under the third base or base 3. In a preferred embodiment, the SNP or other mismatch is located under base 2, the second base from the 3' end also called the penultimate base.

SNP differentiation has been analyzed with the mismatch under base 1 and base 3, but not under base 2. Since the ΔCt between wild type and mismatch for co-primers with the mismatch located under base 1 and base 3 were similar and small, it was surprising to discover that the ΔCt increased dramatically with the mismatch under base 2, the penultimate base.

The gap size is the number of bases between the 3' end of the first sequence and the 5' end of the second sequence in the co-primer. Gap sizes are unique to co-primers since normal primers do not have a second sequence which folds over the primer to bind downstream from the 3' end of the first sequence. The presence of the gap provides a unique benefit to co-primers in differentiation of SNP's and other polymorphisms. Without being limited by theory, small gaps of 3, 2, 1, 0, or fewer bases create steric hindrance for the binding of the polymerase to the 3' end of the first sequence. The presence of steric hindrance increases specificity of the already strained initial binding/extension event where a mismatch is present. In a preferred embodiment, the gap size is 2 or fewer bases. In a still more preferred embodiment, the gap size is 1 or fewer bases.

Using a gap size of 2 or fewer bases was previously contraindicated. Data collected by the researchers, both published and unpublished, indicated that amplification efficiency was most likely to be maximized with a gap size of at least 3 bases. Decreasing the number of bases in the gap was increasingly contraindicated based on data. Thus, the results finding that gap size is significant in co-primer differentiation of SNP's and other polymorphisms is surprising. For example, a previously published research (Co-operative Primers: Intersecting Spherical Model for the Optimization of Linker and Gap Lengths) states, "In the case of a short gap, lack of perfect flexibility in the template leads to competition between the polymerase and the capture for space. Also, the polymerase cannot begin extending without immediate resistance from the capture sequence being bound." This paper theorizes a 'penalty' to amplification efficiency due to short gap lengths.

A further feature unique to co-primers is the ability to create a "negative gap." A negative gap is where the 3' end of the first sequence overlaps the 5' end of the second sequence in the co-primer. An overlap of a single base would correspond to a gap size of −1. An overlap of two, three, four, or five bases would correspond to gap sizes of −2, −3, −4, and −5 bases respectively.

In some embodiments, negative gap sizes are −1, −2, −3, −4, −5 or fewer bases. Without being bound by theory, this adds competition to binding in addition to steric hindrance leading to even greater specificity. In a preferred embodiment, gap size is −1 or −2 bases. As with small gap sizes, negative gaps are contraindicated and their use to enhance specificity is surprising.

In embodiments where the gap size is negative such that the SNP or target mismatch is contained in the target binding areas of both the priming sequence and the capture sequence, a preferred method is to design the primer as described above to target the SNP, while the corresponding nucleotide on the capture sequence is designed opposite such that it is complementary to the differing strand or the opposite polymorphism to the priming sequence. For example, if the priming sequence is made complementary to the Wild Type strain and the SNP target nucleotide is complementary to that strain, then the SNP target nucleotide of the capture sequence will be complementary to the Mutant Strain, and vice versa. In this embodiment, the priming sequence and capture sequence compete for their relative complementary target. If the Wild Type strain is present, the priming sequence has the advantage over the capture sequence and extension occurs. If only the mutant strain is present, the capture sequence wins out and no extension occurs since the 3' end of the primer are unbound.

In some embodiments, competing co-primers for the other allele or mismatch are present. Without being bound by theory, the presence of competing primers creates competition for the reverse primer leading to an increase in specificity. For example, if the co-primer designed targets the wildtype, then the competing co-primer would target the mutant. Amplification of the mutant by the co-primer would reduce the amount of reverse primer present leading to less amplification efficiency for the wildtype primer when it begins to amplify. In previous work, the competing primers were not introduced to the SNP differentiation process. The increase in ΔCt by adding competing co-primers was surprising.

In some embodiments, the Tm of the first sequence in the co-primer is more than 0, 1, 2, 3, 4, 5, 6, 7, 8, 9, 10, 11, 12, 13, 14, 15, 16, 17, 18, 19, 20, 21, 22, 23, 24, 25 C below the reaction temperature. In some embodiments the second sequence in the co-primer is more than 0, 1, 2, 3, 4, 5, 6, 7, 8, 9, 10, 11, 12, 13, 14, 15, 16, 17, 18, 19, 20, 21, 22, 23, 24, 25 C below the reaction temperature.

In some embodiments, additional mismatches are intentionally created in the first or second sequence in the co-primer. In a preferred embodiment, an additional 1, 2, 3, 4, 5, 6, 7, 8, 9, 10 mismatches are added to the 5' end of the first sequence such that the predicted Tm is lower for the initial round of binding and amplification but increases on the second and all subsequent rounds of amplification. In other embodiments, one or more mismatches are intentionally added to other locations in the first priming sequence. In some embodiments, the master mix used enhances SNP or other mismatch differentiation.

In some embodiments, each of the factors: (i.e., 1) the placement of the SNP or other mismatch on the first or priming sequence in the co-primer; 2) the gap size or number of nucleic acids between the 3' end of the extendable first sequence and the 5' end of the second sequence; 3) the presence of competing co-primers for the other allele; 4) the Tm of the first and/or second sequence relative to the reaction temperature; 5) the addition of other mismatches intentionally placed in the first and/or second sequence; and 6) the type of master mix used) are used alone to enhance SNP differentiation. In preferred embodiments, two or more factors are used in combination to increase specificity beyond the sum of the parts.

For example, in a preferred embodiment, the mutation is located under the penultimate base of the first sequence and the gap size is restricted to 2, 1, 0, −1, −2, −3 or fewer bases. In other embodiments, the mutation is located under the penultimate base of the first sequence and competing primers for the other allele are present. In still other embodiments, the mutation is located under the penultimate base of the first sequence and the Tm of the first sequence is more than 5° C. below the reaction temperature. In still other embodiments, the mismatch is under the penultimate base of the first sequence and additional mismatches are added to the 5' end of the first sequence.

In still other embodiments, the gap size is 2, 1, 0, −1, −2, −3 or fewer bases and competing co-primers are present. In yet other embodiments, the gap size is 2, 1, 0, −1, −2, −3 or fewer bases and the Tm of the first sequence is more than 5° C. below the reaction temperature. In still other embodiments, the gap size is 2, 1, 0, −1, −2, −3 or fewer bases and additional mismatches are intentionally added on the 5' end of the first sequence. In still more preferred embodiments, three or more factors may be combined together. For example, in one such preferred embodiment, the mutation is located under the penultimate base, the gap size is 2, 1, 0, −1, −2, −3 or fewer bases, and competing co-primers are present. In still other embodiments, 4, 5, or even all 6 factors are present together.

The target nucleic acid and differing nucleic acid can differ by 1, 2, 3, 4, 5, 6, 7, 8, 9, 10, 11, 12, 13, 14, 15, 16, 17, 18, 19, 20, or more nucleotides. For example, the differing nucleic acid can comprise a single nucleotide morphism (SNP) when compared to the target nucleic acid. Also disclosed is a multiplex assay, discussed in detail below, with multiple differing nucleic acids that can differ from the target nucleic acid by 1, 2, 3, 4, 5, 6, 7, 8, 9, 10, 11, 12, 13, 14, 15, 16, 17, 18, 19, 20, or more nucleotides. When more than one nucleotide differs between the target and differing nucleic acid, the different nucleotides may be contiguous, or may be non-contiguous. When they are non-contiguous, they may be separated by 1, 2, 3, 4, 5, 6, 7, 8, 9, 10, 11, 12, 13, 14, 15, 16, 17, 18, 19, 20, 30, 40, 50, 60, 70, 80, 90, 100, or more nucleotides, or any amount above or in between these amounts.

The target nucleic acid and the differing nucleic acid can differ by not only a substitution, but can also be the result of an insertion or deletion. One of skill in the art will appreciate that any difference between the target nucleic acid and the differing nucleic acid can be exploited to amplify the target over the differing nucleic acid.

In the present invention, the target nucleic acid is synthesized preferentially to the differing nucleic acid allowing it to be amplified much more than the differing nucleic acid. In the present invention, "synthesizing the target nucleic acid and not synthesizing the differing nucleic acid" means that, for all practical purposes known in the art, the target nucleic acid is amplified to a much greater degree. For example, the target nucleic acid can be synthesized 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, or 2000-fold or more when compared with the differing nucleic acid (or any amount above or between).

Preferential synthesis can occur with a single round of nucleic acid synthesis or can be used in multiple rounds. In one embodiment, a single round of synthesis might be used as part of a method to preferentially sequence a target nucleic acid.

In some embodiments, differentiation of the target nucleic acid is desired during or following amplification. For example, in some embodiments employing real-time detection the ΔCt between the target and differing nucleic acid is 3, 4, 5, 6, 7, 8, 9, 10, 11, 12, 13, 14, 15, 16, 17, 18, 19, 20, or more cycles. In a preferred embodiment, the ΔCt is 10 or more cycles. In a more preferred embodiment, the ΔCt is 15 or more cycles. In some embodiments, only the target nucleic acid has a measurable Ct.

In other embodiments, end-point detection methods are used to determine quantity of the target nucleic acid relative to the differing nucleic acid. In some embodiments, gel or capillary electrophoresis is used. In other embodiments, fluorescence is measured. In still others, signals known to those skilled-in-the-art are measured.

Figure 13:
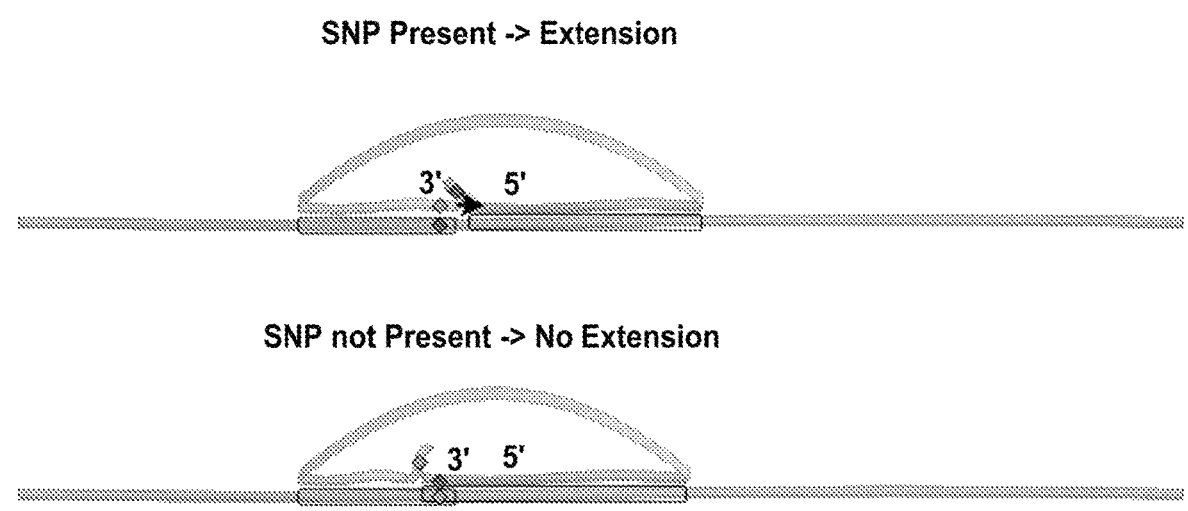
FIG. 13 shows a Cooperative Primer made to target a SNP. The capture sequence is also made so that the targets of the primer and capture overlap. The capture sequence is made with a nucleotide targeting the opposite SNP of the primer. If the targeted SNP is present, the 5' end of the capture does not bind, while the 3' end of the primer does, which results in polymerase extension. If the targeted SNP is not present, the 5' end of the capture hybridizes to the target which further reduces the possibility of the 3' end of the primer to bind, and no polymerase extension occurs.

In one embodiment, the complementarity between the second nucleic acid sequence can be within one nucleotide of the first region of the target nucleic acid. The complementarity between the second nucleic acid sequence and first region of the target nucleic acid can also be contiguous, such that there are no nucleotides, or "gaps" between these two regions. Alternatively, there can exist overlap between the second nucleic acid sequence and the first region of the target nucleic acid, such that 1, 2, 3, 4, 5, or more nucleotides overlap. An example of this can be seen in FIG. 13.

Multiple cooperative nucleic acids can be used in the assay. For example, there can be 2, 3, 4, 5, 6, 7, 8, 9, 10, 11, 12, 13, 14, 15, 16, 17, 18, 19, 20, 30, 40, 50, 60, 70, 80, 90, 100, or more different cooperative nucleic acids in the same assay. These different cooperative nucleic acids can be directed to any amount of target nucleic acids in the sample. For example, different cooperative nucleic acids that are complementary to various strains of the same bacteria can be used. Alternatively, different cooperative nucleic acids that are complementary to various SNPs can be used. In this case, a second, third, and even a fourth cooperative nucleic acid could be used simultaneously to detect different nucleotide combinations present in a SNP. For example, the first cooperative nucleic acid can be specific for an "A" base in a SNP, the second cooperative nucleic acid could be specific for a "T" base in a SNP, a third cooperative nucleic acid could be specific for a "C" base in a SNP, and a fourth cooperative nucleic acid could be specific for a "G" base in a SNP. These different cooperative nucleic acids can be exposed simultaneously to the target nucleic acids, or can be exposed at different times in different assays. In one embodiment, the first and second cooperative nucleic acids can amplify their intended targets under substantially similar conditions. In another embodiment, the conditions can vary, thereby allowing one target nucleic acid to be amplified differentially than the other target nucleic acid based on assay conditions.

Also disclosed is a multiplex assay wherein the first nucleic acid sequence of the cooperative nucleic acid molecule will not hybridize to the target nucleic acid without the second nucleic acid sequence hybridizing to the target nucleic acid. This is referred to herein as "conditional hybridization."

Furthermore, increasing the length of a primer or sequence of nucleotides increases its melting temperature, or Tm, defined as the temperature at which 50% of available sequences are hybridized. Generally, increasing Tm increases sensitivity but reduces specificity. Given favorable conditions, primers can bind and extend on any nucleotides present in a sample. Increasing specificity will reduce the efficiency at which they bind and extend to anything besides the desired target. This is called non-specific binding, non-specific extension, or non-specific amplification. The purpose of increasing specificity is to decrease non-specific binding, extension, and amplification.

One type of non-specific binding can occur when a primer binds to another primer. If extension occurs, the product is called a primer-dimer. Primer-dimers are an especially dangerous non-specific product because they constitute an exact complement to a primer since extension occurred across a primer present in the reaction. Because of this, that primer will bind and extend at full efficiency to that primer-dimer throughout the remainder of the reaction. In a PCR application, any primer dimer formed will amplify exponentially throughout the reaction and may generate false signal, eclipse true signal, or decrease true signal by using up reagents that would otherwise have been utilized in desired amplification purposes.

The "Cooperative Primer," alternatively referred to herein as a "Cooperative Nucleic Acid," refers to a primer that is much shorter than traditional primers. Generally, the Tm of this primer is too low for the primer to bind, extend, or amplify by itself in a reaction. This gives the Cooperative Primer extremely high specificity. The primer is unable to bind to non-specific targets efficiently, which drastically reduces non-specific product formation. Regarding primer dimers, the advantage is amplified by the fact that not only are primer dimers less likely to form, but even after they form their Tm is too low to facilitate future binding, extension, and amplification of the primer dimers. The extremely short and highly specific primer of the Cooperative Primer would have very low sensitivity if it were not for the linker and capture. The capture is a nucleotide sequence with Tm at or near or above reaction temperature. The capture is linked to the primer by a flexible, non-extendable linker attached to the 5' end of the primer and either the 3' or 5' end of the capture. Generally, the capture is not extendable due to either the linker or a fluorescent label attached to its 3' end. The capture, with its Tm near reaction temperature, is able to bind to its target. The capture target is generally near the primer target so that when the capture hybridizes to its target, the primer by virtue of the linker is brought into artificially close proximity to its target. This increases the local concentration of the primer, which increases its effective Tm to the target in the vicinity, facilitating binding and extension. Since the linker blocks extension, any non-specific product or primer dimer will not contain both the primer and capture targets, which will eliminate possible future amplification of that product. In this way, cooperative primers can maintain an extremely high level of specificity while still being sensitive enough to amplify the desired target.

The cooperative nucleic acids of the present invention are in sharp contrast with concepts such as the dual specificity primer (US Patent Publication 20120135473, herein incorporated by reference in its entirety for its teaching concerning dual specificity primers). See Example 6, The dual specificity primer has a capture sequence linked to a short primer via Inosine residues where the capture sequence hybridizes to the target on the 5' side of the primer. The result is that the dual specificity primer is highly specific in the first round of amplification. However, if the dual specificity primers amplify each other, the polymerase extends all the way through to the 5' end, creating a high Tm primer-dimer that will be propagated in every round thereafter. This is in contrast to the cooperative nucleic acid where the capture sequence hybridizes to the target on the 3' side of the primer, preventing it from being incorporated into the primer-dimer in the order necessary to allow for propagation of the primer-dimer.

The cooperative nucleic acids and methods of using them are also different than "padlock probes" (Nilsson et al. 1994: "Padlock probes: circularizing oligonucleotides for localized DNA detection". Science 265 (5181): 2085-2088), Molecular Inversion Probes (MIPs) (Hardenbol et al 2003: "Multiplexed genotyping with sequence-tagged molecular inversion probes". Nat Biotechnol 21 (6): 673-678) and Connector Inversion Probes (CIPs) (Akhras et al. 2007: Hall, Neil. ed. "Connector inversion probe technology: a powerful one-primer multiplex DNA amplification system for numerous scientific applications". PLoS ONE 2 (9): e195). For example, the probes disclosed herein can have a linker with at least one non-extendable moiety. Furthermore, the molecule disclosed herein is a primer, whereas the "padlock probes" are ligated, and the non-ligated padlock probes are digested or otherwise removed prior to amplification and cannot be used as primers.

Padlock probes are single stranded DNA molecules with two 20-nucleotide long segments complementary to the target connected by a 40-nucleotide long linker sequence. When the target complementary regions are hybridized to the DNA target, the padlock probes also become circularized. However, unlike MIP, padlock probes are designed such that the target complementary regions span the entire target region upon hybridization, leaving no gaps. Thus, padlock probes are only useful for detecting DNA molecules with known sequences.

Molecular Inversion probes were developed to perform SNP genotyping, which are modified padlock probes such that when the probe is hybridized to the genomic target, there is a gap at the SNP position. Gap filling using a nucleotide that is complementary to the nucleotide at the SNP location determines the identity of the polymorphism. This design brings numerous benefits over the more traditional padlock probe technique. Using multiple padlock probes specific to a plausible SNP requires careful balancing of the concentration of these allele specific probes to ensure SNP counts at a given locus are properly normalized.

Connector Inversion Probes make use of a modified design of MIP by extending the gap delimited by the hybridized probe ends and named the design Connector Inversion Probe (CIP). The gap corresponds to the genomic region of interest to be captured (e.g. exons). Gap filling reaction is achieved with DNA polymerase, using all four nucleotides. Identification of the captured regions can then be done by sequencing them using locus-specific primers that map to one of the target complementary ends of the probes.

The present invention also relates to cooperatively linked nucleic acids that also comprise a probe. This modified primer/probe is similar to the cooperative nucleic acid, but with the addition of one or more detectable labels to either the capture sequence or the primer, turning it into a probe. Because extension of the cooperative primer/probe is detectable, it can be useful in a variety of applications including multiplexing applications that require differentiation of SNP's using an ARMS based approach. In some embodiments, both the primer and the probe are designed with Tm's below the melting temperature which is used in the amplification reaction, so that the primer will not amplify without the probe binding and the probe will not have a signal without the primer binding. This creates two points of specificity in the same primer/probe combination.

The cooperative nucleic acids, such as primers and probes, of this invention are useful in a variety of primer extension/amplification reactions known to those skilled in the art, including, but not limited to the polymerase chain reaction, rolling circle amplification, nucleic acid sequencing and others. The cooperative primers and probes of this invention can also be used in applications that have post extension/amplification steps, such as hybridization to an array. Because the cooperative primers/probes in this invention substantially reduce primer-dimers, they are of particular use in multiplexed and highly multiplexed reactions.

The use of a cooperative nucleic acid can decrease the amount of primer-dimer present by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent compared to the amount of primer-dimer present when a normal primer (a non-cooperative nucleic acid) is used.

The cooperative nucleic acid may be linear or circularized.

By "extendable on the 3' end" is meant that the first nucleic acid is free on this end to be amplified, or extended. This is meant to include heat activatable primers such as those described by Lebedev et al, among other technologies.

In one example, the cooperative nucleic acid comprises 75, 70, 65, 60, 55, 50, 45, 40, 35, 30, 25, 20, 15, 10, or less continuous nucleotides in the same orientation. In other words, this is the number of nucleotides that are part of a single, unbroken nucleic acid sequence and oriented in the same 5' to 3' direction, or the 3' to 5' direction. By way of example, if the linker is a nucleic acid sequence, it can include the linker, if the nucleotides in the linker are in the same orientation as either the first or second nucleic acid sequence to which it is directly connected.

The linker can be made of nucleic acids, non-nucleic acids, or some combination of both. If the linker is made of nucleic acids, it can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 or more nucleotides in length, or any number in between. Types of linkers are discussed elsewhere herein. The linker can be any length, and can be longer or shorter than the combined length of the first and second nucleic acid sequences, longer or shorter than just the first nucleic acid sequence, or longer or shorter than the second nucleic acid sequence. The linker can be made so that it is non-extendable.

Also disclosed herein is a kit comprising the cooperative nucleic acid molecules disclosed herein together with instructions for their use. In some embodiments, additional cooperative nucleic acid molecules are provided in the kit. In still others, reagents for performing the extension are included, such as polymerase, dNTP's, buffers and the like. In some embodiments, positive and negative controls may be included. In such embodiments, the reagents may all be packaged separately or combined in a single tube or container.

Primer Design

In some embodiments, the isolated melting temperature "Tm" of the primer, also referred to herein as the first nucleic acid sequence, is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more degrees below the reaction temperature used during the annealing phase, of PCR, or the extension phase of reactions with no annealing phase. Therefore, the melting temperature of the primer sequence can be between about 1° C. and 40° C., between about 3° C. and 20° C., between about 5° C. and 15° C. below the reaction temperature used in the PCR reaction. In a preferred embodiment, the isolated Tm is between about 7° C. and 12° C. below the reaction temperature. This provides for less than 20%, and more preferably less than 5% of the template to be hybridized to an isolated primer.

One of skill in the art can design primers with a given melting temperature based on many factors, such as length, and with increasing GC content. A simple formula for calculation of the (Tm) is:

$$Tm = 4(G+C) + 2(A+T)° \text{ C.}$$

Furthermore, one of skill in the art will appreciate that the actual Tm is influenced by the concentration of $Mg^{2+}$, $K^+$, and cosolvents. There are numerous computer programs to assist in primer design.

To achieve the desired melting temperatures, the first nucleic acid sequence, or the primer, can be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 bases in length. For example, the primers can be between about 5 and 26, between about 7 and 22, between about 9 and 17 bases in length depending on GC content.

Any desired number of primers of different nucleotide sequence can be used, but use of one or a few primers is preferred. The amplification reaction can be performed with, for example, one, two, three, four, five, six, seven, eight, nine, ten, eleven, twelve, thirteen, fourteen, fifteen, sixteen, or seventeen primers. More primers can be used. There is no fundamental upper limit to the number of primers that can be used. However, the use of fewer primers is preferred. When multiple primers are used, the primers should each have a different specific nucleotide sequence.

The amplification reaction can be performed with a single primer and, for example, with no additional primers, or with 1 additional primer, with 2 additional primers, with 3 additional primers, with 4 additional primers, with 5 additional primers, with 6 additional primers, with 7 additional primers, with 8 additional primers, with 9 additional primers, with 10 additional primers, with 11 additional primers, with 12 additional primers, with 13 additional primers, with 14 additional primers, with 15 additional primers, with 16 additional primers, with 17 additional primers, with 18 additional primers, with 19 additional primers, with 20 additional primers, with 21 additional primers, with 22 additional primers, with 23 additional primers, with 24 additional primers, with 25 additional primers, with 26 additional primers, with 27 additional primers, with 28 additional primers, with 29 additional primers, with 30 additional primers, with 31 additional primers, with 32 additional primers, with 33 additional primers, with 34 additional primers, with 35 additional primers, with 36 additional primers, with 37 additional primers, with 38 additional primers, with 39 additional primers, with 40 additional primers, with 41 additional primers, with 42 additional primers, with 43 additional primers, with 44 additional primers, with 45 additional primers, with 46 additional primers, with 47 additional primers, with 48 additional primers, with 49 additional primers, with 50 additional primers, with 51 additional primers, with 52 additional primers, with 53 additional primers, with 54 additional primers, with 55 additional primers, with 56 additional primers, with 57 additional primers, with 58 additional primers, with 59 additional primers, with 60 additional primers, with 61 additional primers, with 62 additional primers, with 63 additional primers, with 64 additional primers, with 65 additional primers, with 66 additional primers, with 67 additional primers, with 68 additional primers, with 69 additional primers, with 70 additional primers, with 71 additional primers, with 72 additional primers, with 73 additional primers, with 74 additional primers, with 75 additional primers, with 76 additional primers, with 77 additional primers, with 78 additional primers, with 79 additional primers, with 80 additional primers, with 81 additional primers, with 82 additional primers, with 83 additional primers, with 84 additional primers, with 85 additional primers, with 86 additional primers, with 87 additional primers, with 88 additional primers, with 89 additional primers, with 90 additional primers, with 91 additional primers, with 92 additional primers, with 93 additional primers, with 94 additional primers, with 95 additional primers, with 96 additional primers, with 97 additional primers, with 98 additional primers, with 99 additional primers, with 100 additional primers, with 110 additional primers, with 120 additional primers, with 130 additional primers, with 140 additional primers, with 150 additional primers, with 160 additional primers, with 170 additional primers, with 180 additional primers, with 190 additional primers, with 200 additional primers, with 210 additional primers, with 220 additional primers, with 230 additional primers, with 240 additional primers, with 250 additional primers, with 260 additional primers, with 270 additional primers, with 280 additional primers, with 290 additional primers, with 300 additional primers, with 310 additional primers, with 320 additional primers, with 330 additional primers, with 340 additional primers, with 350 additional primers, with 360 additional primers, with 370 additional primers, with 380 additional primers, with 390 additional primers, with 400 additional primers, with 410 additional primers, with 420 additional primers, with 430 additional primers, with 440 additional primers, with 450 additional primers, with 460 additional primers, with 470 additional primers, with 480 additional primers, with 490 additional primers, with 500 additional primers, with 550 additional primers, with 600 additional primers, with 650 additional primers, with 700 additional primers, with 750 additional primers, with 800 additional primers, with 850 additional primers, with 900 additional primers, with 950 additional primers, with 1,000 additional primers, with 1,100 additional primers, with 1,200 additional primers, with 1,300 additional primers, with 1,400 additional primers, with 1,500 additional primers, with 1,600 additional primers, with 1,700 additional primers, with 1,800 additional primers, with 1,900 additional primers, with 2,000 additional primers, with 2,100 additional primers, with 2,200 additional primers, with 2,300 additional primers, with 2,400 additional primers, with 2,500 additional primers, with 2,600 additional primers, with 2,700 additional primers, with 2,800 additional primers, with 2,900 additional primers, with 3,000 additional primers, with 3,500 additional primers, or with 4,000 additional primers. The additional primers can be additional cooperative primers, or can be traditional (linear) primers.

The disclosed primers can have one or more modified nucleotides. Such primers are referred to herein as modified primers. Chimeric primers can also be used. Chimeric primers are primers having at least two types of nucleotides, such as both deoxyribonucleotides and ribonucleotides, ribonucleotides and modified nucleotides, two or more types of modified nucleotides, deoxyribonucleotides and two or more different types of modified nucleotides, ribonucleotides and two or more different types of modified nucleotides, or deoxyribonucleotides, ribonucleotides and two or more different types of modified nucleotides. One form of chimeric primer is peptide nucleic acid/nucleic acid primers. For example, 5'-PNA-DNA-3' or 5'-PNA-RNA-3' primers may be used for more efficient strand invasion and polymerization invasion. Other forms of chimeric primers are, for example, 5'-(2'-O-Methyl) RNA-RNA-3' or 5'-(2'-O-Methyl) RNA-DNA-3'.

Many modified nucleotides (nucleotide analogs) are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and 0-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. A primer having one or more universal bases is not considered to be a primer having a specific sequence.

Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[(CH$_2$)n O]m CH$_3$, —O(CH$_2$)n OCH$_3$, —O(CH$_2$)n NH$_2$, —O(CH$_2$)n CH$_3$, —O(CH$_2$)n —ONH$_2$, and —O(CH$_2$)nON[(CH$_2$)n CH$_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate nucleic acid molecules.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., *Science* 254:1497-1500 (1991)).

Primers can be comprised of nucleotides and can be made up of different types of nucleotides or the same type of nucleotides. For example, one or more of the nucleotides in a primer can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides;

about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. The nucleotides can be comprised of bases (that is, the base portion of the nucleotide) and can (and normally will) comprise different types of bases.

Capture Sequence Design

The capture sequence, also referred to herein as the "second nucleic acid sequence," is complementary to the template such that it hybridizes to the target nucleic acid molecule downstream from the 3' end of the primer. In some embodiments, resistance to mutations in the target nucleic acid is desired and the capture sequence is designed with a melting temperature greater than the reaction temperature. In these embodiments, the capture sequence is designed with an isolated Tm of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more degrees above the reaction temperature. For example, the capture, or second, sequence is between about 0° C. and 40° C., between about 5° C. and 30° C., between about 7° C. and 25° C. above the reaction temperature. In some embodiments, the predicted melting temperature of the capture sequence is also made for expected mutants. In these embodiments, the isolated Tm of the capture sequence to the expected mutants is between about 1, 2, 3, 4, 5, 6, 7, 8, 9, 10, 11, 12, 13, 14, 15 16, 17, 18, 19, 20, or more degrees C. below the reaction temperature, or 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 or more degrees C. above the reaction temperature. For example, it can be 10° C. below the reaction temperature and 30° C. above the reaction temperature, between about 3° C. below the reaction temperature and about 10° C. above the reaction temperature.

To achieve these melting temperatures, the capture sequence length can be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 or more bases in length. For example, it can be between about 20 and about 50, between about 22 and about 40, between about 23 and about 37 bases.

In some embodiments, an even higher resistance to mutations in the target sequence is desired. In these embodiments, in addition to a capture sequence with an isolated Tm of between about 0° C. and 40° C. above the reaction temperature, the cooperative primer is designed with an isolated Tm of between about 7° C. below and about 20° C. above, between about 5° C. below and about 10° C. above, between about 3° C. below and about 3° C. above the reaction temperature. The cooperative interaction between the primer and the capture sequence will result in an even greater effective Tm for the cooperative primer, rendering it almost impervious to mutations in the sequence. By comparison, a normal primer might have to be an additional 5 to 30 bases in length to have an equivalent resistance to mutations in the target sequence, and consequently, would be much more susceptible to primer-dimer formation.

In other embodiments, a higher resistance to primer-dimers is preferred and the melting temperature of the isolated capture, or second, nucleic acid sequence is designed to be less than the reaction temperature. For example, the capture, or second, nucleic acid sequence is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more degrees below the reaction temperature, or annealing phase, of PCR. In preferred embodiments, the Tm of the isolated capture, or second nucleic acid, sequence is between about 0° C. and 12° C., between about 1° C. and 8° C., between about 2° C. and 5° C. below the reaction temperature. To achieve these low melting temperatures, the capture sequence length can be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more bases in length. For example, the capture, or second nucleic acid sequence, can be between about 5 and 30, between about 8 and 25, and between about 10 and 22 bases.

In some embodiments, the capture sequence binds and releases the target sequence rapidly such that the polymerase can extend underneath the capture sequence, leaving the capture sequence intact. In some embodiments, this is enhanced using a cooperative primer with the linker attached to the 5' end of the capture sequence. In a preferred embodiment, the polymerase is capable of cleaving the capture sequence during extension. In a preferred embodiment, this is enhanced using a cooperative primer with the linker attached to the 3' end of the capture sequence.

Linker

The number of bases between the 3' end of the first nucleic acid, or primer, sequence and the 5' end of the second nucleic acid, or capture sequence hybridization locations in the template is important. In some embodiments, the number of bases between the primer and the capture sequence is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. For example, they can be between about 0 and 30, between about 0 and 20, between about 0 and 10 bases.

The more bases that are between the two sites, the longer the linker needs to be if cleavage of the capture sequence is desired. The longer the linker, the more entropy that enters into the system, which lowers the effect of cooperative binding. This is expressed in the following equation:

$$K_{eff} = K_{primer} + K_{capture} + L_C K_{primer} K_{capture}$$

Where $K_{eff}$ is the effective or cooperative equilibrium constant, $K_{primer}$ is the equilibrium constant of the primer in isolation, $K_{capture}$ is the equilibrium constant of the capture sequence in equilibrium and $L_c$ is the local concentration defined as:

$$L_C = \frac{\left(\frac{1}{6.022E23}\right)}{\frac{4}{3}\pi r^3}$$

Where r is the linker length in decimeters. This provides the effective local concentration in molarity due to the cooperative interaction between the primer and the probe. Accordingly, linker length directly determines the cooperative contribution ($L_c K_{primer} K_{capture}$) to the effective equilibrium constant.

$K_{primer}$ and $K_{capture}$ can be calculated by obtaining the enthalpy and entropy values for the primer and the capture sequences using nearest neighbor or other calculations known to those skilled in the art.

The total amount of template bound by the primer can be calculated as follows:

$$\frac{T_{primer}}{T_o} = \frac{(K_{primer} + L_C K_{primer} K_{capture}) P_o}{1 + (K_{primer} + K_{capture} + L_C K_{primer} K_{capture}) P_o}$$

Where Tprimer is the template bound by primer, To is the total amount of template and $P_o$ is the starting cooperative primer concentration. It can be seen that the cooperative effect is greatest when $L_C K_{primer} K_{capture}$ is much greater than $K_{primer}$. For this to occur the linker length should be as short as possible.

While the math shows that the linker length should be as short as possible, there are several limitations to how short the linker can actually be. When the capture sequence and the probe bind to the template, they form rigid double helices. The linker length must be sufficient to accommodate this structure.

Figure 8:
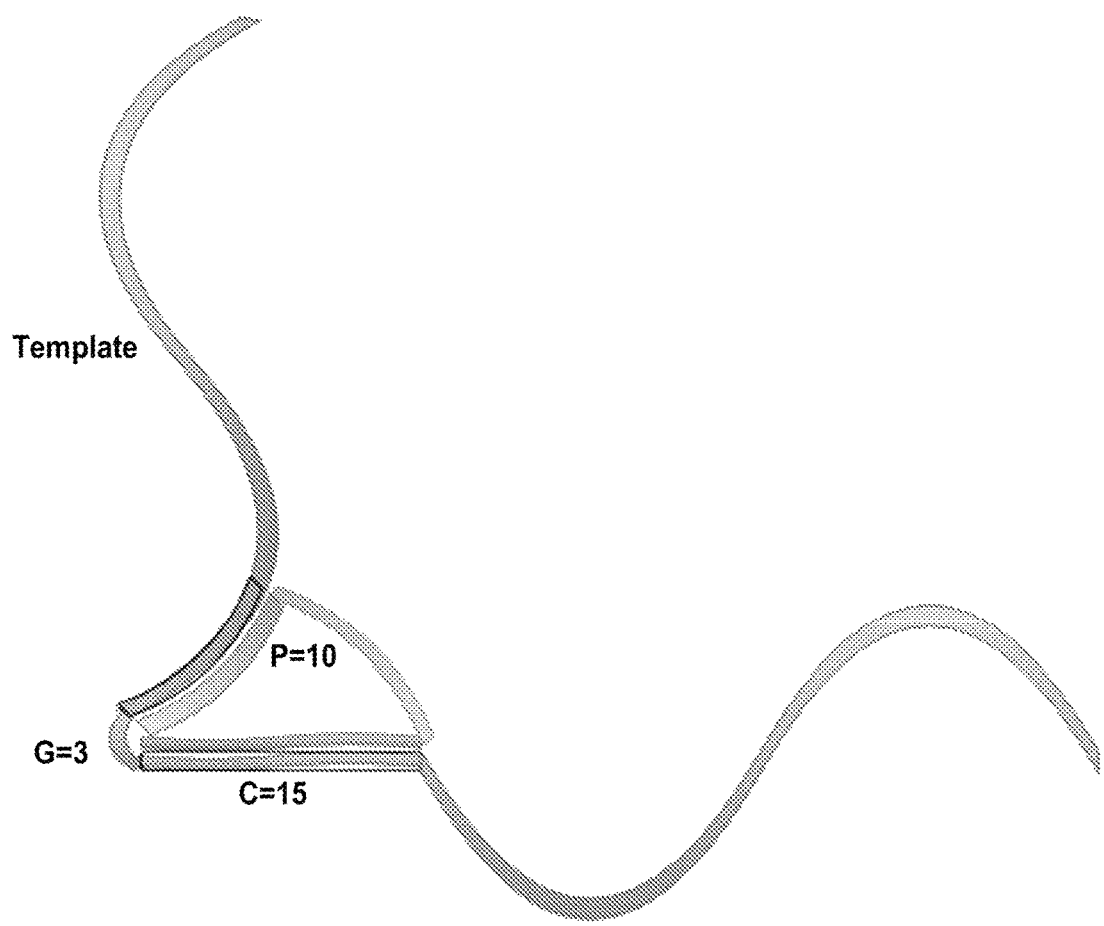
FIG. 8 is a roughly to-scale figure showing a Cooperative Primer bound to its target. Units are in nucleotide-length. A primer (blue) is shown about 10 nucleotides in length hybridized to its target. A capture (purple) is shown about 15 nucleotides in length hybridized to its target. A linker is shown (green) about 12 nucleotides in length connecting the primer and capture. The template (red) has a roughly 3 nucleotide gap between the primer target and capture target.
Figure 9:
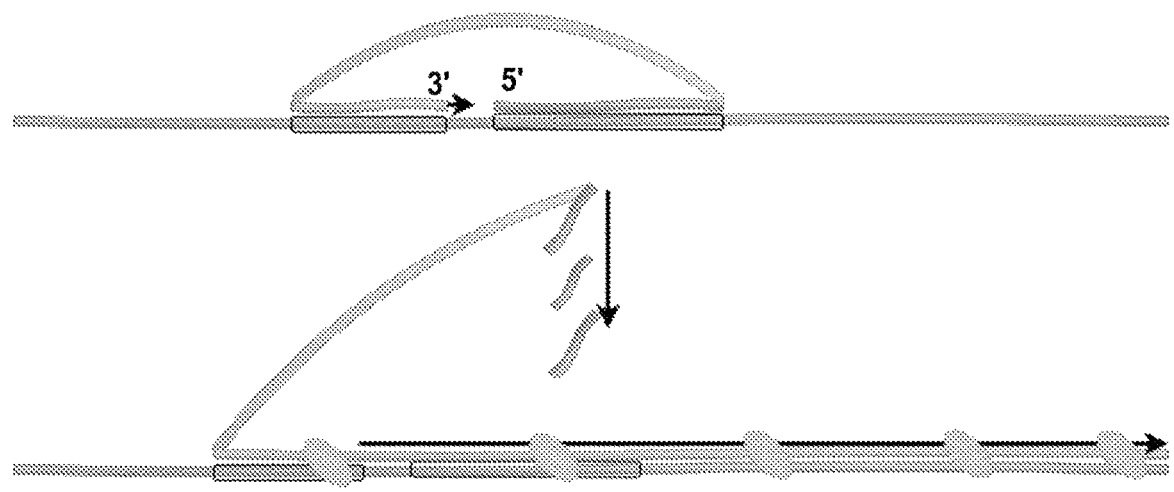
FIG. 9 shows a method of detection of Cooperative Primer amplification using intercalating dye. The Cooperative Primer, upon hybridization and extension, forms double stranded DNA. The intercalating dye then inserts itself into that double-stranded helix and increases in fluorescent signal. This increase in fluorescent signal can then be detected.
Figure 10:
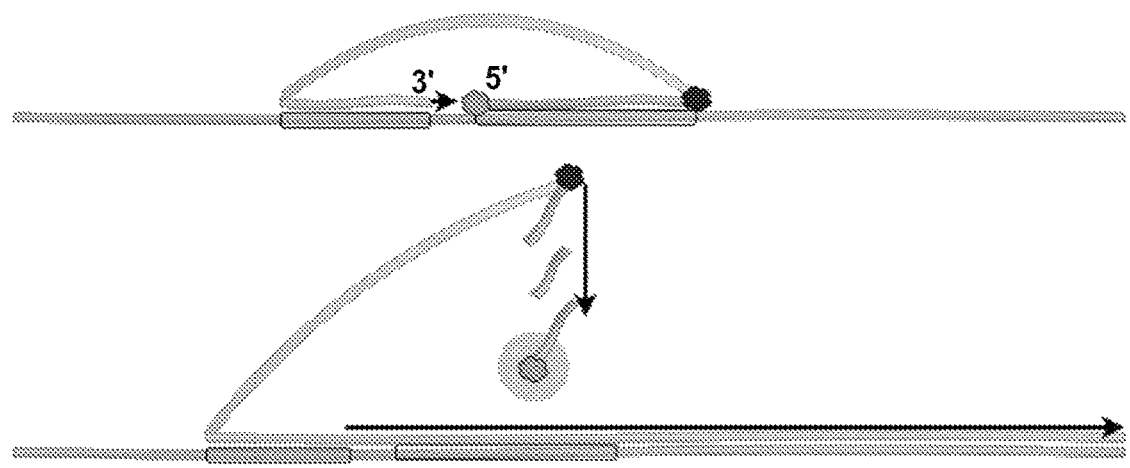
FIG. 10 shows a method of detection of Cooperative Primer amplification using a fluorescent label. The Cooperative Primer is labeled with a fluorescent label (green) and quencher (violet). The label and quencher are in close proximity and fluorescence is muted. Upon hybridization and extension, the polymerase cleaves the capture, releasing the fluorescent label and increasing its distance from the quencher. This increases fluorescent signal which can then be detected.
Figure 11:
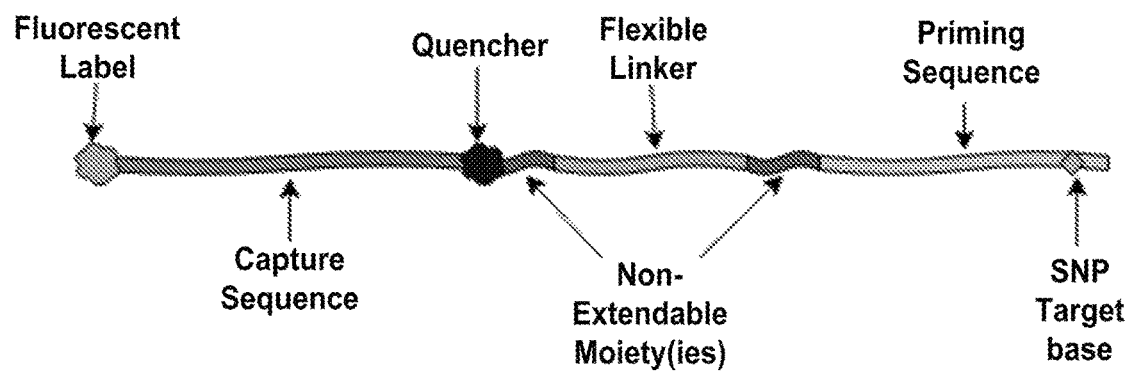
FIG. 11 shows a Cooperative Primer made to target a SNP. All parts are labeled. The Cooperative Primers is oriented from 5' to 3' direction.
Figure 12:
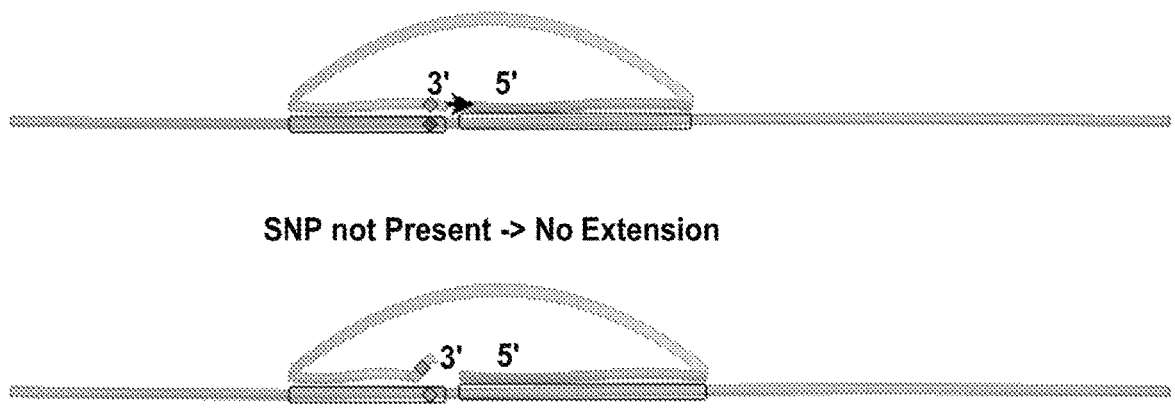
FIG. 12 shows a Cooperative Primer made to target a SNP. The nucleotide made to target the SNP is labeled in orange. When the Cooperative Primer binds to a target that contains the SNP that is targeted, the 3' end of the primer binds and the polymerase is able to extend. If the targeted SNP is not present, the 3' end of the primer does not bind—even if the rest of the Cooperative Primer does—and no polymerase extension occurs.

In some embodiments, the linker attaches the 5' end of the primer to the 3' end of the capture sequence (FIGS. 1-3, 6, 7, 9, 10, 12, and 13). In this embodiment, the linker is larger than the combined length of the primer and capture sequences. In a preferred embodiment where the linker attaches to the 3' end of the capture sequence, the linker comprises 6 hexaethylene glycols. In another embodiment, the primer is inverted such that the 5' end of the primer is attached to the 5' end of the capture sequence. In this embodiment, the linker is longer than the primer. In a preferred embodiment where the linker attaches to the 5' end of the capture sequence, the linker comprises 3 hexaethylene glycols. In yet another embodiment, the 3' end of the capture sequence is linked to the middle of the primer. In this instance, the linker may be shorter than the length of the primer. In other embodiments, the linker may be shorter than described above due to flexibility of the single stranded template (FIG. 8). In such an embodiment, FIGS. 1-3, 6, 7, 9, 10, 12, and 13 are understood to not be drawn "to-scale". Specifically, the linker in the figures is shown to be longer relative to the lengths of the priming and capture sequences than it would be in application.

A variety of linker types and compositions are known to those skilled in the art. Examples include, but are not limited to, polyethylene glycol and carbon linkers. Linkers can be attached through a variety of methods, including but not limited to, covalent bonds, ionic bonds, hydrogen bonding, polar association, magnetic association, and van der wals association. A preferred method is covalent bonding through standard DNA synthesis methods.

The length of polyethylene glycol linkers is about 0.34 nm per monomer. In some embodiments, the length of the polyethylene glycol linker is between about 1 and 90, between about 2 and 50, between about 3 and 30 monomers (between about 1 and 10 nm fully extended).

Using a Primer with a Built-in Detection Mechanism

In some embodiments, the primer has a built-in detection mechanism. In some embodiments the detection mechanism includes one or more detectable labels. In a preferred embodiment, the detection mechanism includes a FRET pair. Examples of primers with built in detection mechanisms include, but are not limited to, Amplifluor primers, Rapid Detex primers, and others known to those skilled in the art.

Cooperative nucleic acids with built in detection mechanisms can be more useful to assay designers than non-cooperative nucleic acids (normal primers) with built in detection mechanisms. Without being limited by theory, this is because cooperative nucleic acids are less prone to generate signal from nonspecific products, such as primer-dimers.

In some embodiments, a nucleic acid binding dye, such as SYBR Green or EvaGreen, is used to monitor the progress of the amplification reaction.

Fluorescent change probes and fluorescent change primers refer to all probes and primers that involve a change in fluorescence intensity or wavelength based on a change in the form or conformation of the probe or primer and nucleic acid to be detected, assayed or replicated. Examples of fluorescent change probes and primers include molecular beacons, Amplifluors, FRET probes, cleavable FRET probes, TaqMan probes, scorpion primers, fluorescent triplex oligos, fluorescent water-soluble conjugated polymers, PNA probes and QPNA probes.

Fluorescent change probes and primers can be classified according to their structure and/or function. Fluorescent change probes include hairpin quenched probes, cleavage quenched probes, cleavage activated probes, and fluorescent activated probes. Fluorescent change primers include stem quenched primers and hairpin quenched primers. The use of several types of fluorescent change probes and primers are reviewed in Schweitzer and Kingsmore, Curr. Opin. Biotech. 12:21-27 (2001). Hall et al., Proc. Natl. Acad. Sci. USA 97:8272-8277 (2000), describe the use of fluorescent change probes with Invader assays.

Hairpin quenched probes are probes that when not bound to a target sequence form a hairpin structure (and, typically, a loop) that brings a fluorescent label and a quenching moiety into proximity such that fluorescence from the label is quenched. When the probe binds to a target sequence, the stem is disrupted, the quenching moiety is no longer in proximity to the fluorescent label and fluorescence increases. Examples of hairpin quenched probes are molecular beacons, fluorescent triplex oligos, and QPNA probes.

Cleavage activated probes are probes where fluorescence is increased by cleavage of the probe. Cleavage activated probes can include a fluorescent label and a quenching moiety in proximity such that fluorescence from the label is quenched. When the probe is clipped or digested (typically by the 5'-3' exonuclease activity of a polymerase during amplification), the quenching moiety is no longer in proximity to the fluorescent label and fluorescence increases. TaqMan probes (Holland et al., Proc. Natl. Acad. Sci. USA 88:7276-7280 (1991)) are an example of cleavage activated probes.

Cleavage quenched probes are probes where fluorescence is decreased or altered by cleavage of the probe. Cleavage quenched probes can include an acceptor fluorescent label and a donor moiety such that, when the acceptor and donor are in proximity, fluorescence resonance energy transfer from the donor to the acceptor causes the acceptor to fluoresce. The probes are thus fluorescent, for example, when hybridized to a target sequence. When the probe is clipped or digested (typically by the 5'-3' exonuclease activity of a polymerase during amplification), the donor moiety is no longer in proximity to the acceptor fluorescent label and fluorescence from the acceptor decreases. If the donor moiety is itself a fluorescent label, it can release energy as fluorescence (typically at a different wavelength than the fluorescence of the acceptor) when not in proximity to an acceptor. The overall effect would then be a reduction of acceptor fluorescence and an increase in donor fluorescence. Donor fluorescence in the case of cleavage quenched probes is equivalent to fluorescence generated by cleavage activated probes with the acceptor being the quenching moiety and the donor being the fluorescent label. Cleavable FRET (fluorescence resonance energy transfer) probes are an example of cleavage quenched probes.

Fluorescent activated probes are probes or pairs of probes where fluorescence is increased or altered by hybridization of the probe to a target sequence. Fluorescent activated probes can include an acceptor fluorescent label and a donor moiety such that, when the acceptor and donor are in proximity (when the probes are hybridized to a target sequence), fluorescence resonance energy transfer from the donor to the acceptor causes the acceptor to fluoresce. Fluorescent activated probes are typically pairs of probes designed to hybridize to adjacent sequences such that the acceptor and donor are brought into proximity. Fluorescent activated probes can also be single probes containing both a donor and acceptor where, when the probe is not hybridized to a target sequence, the donor and acceptor are not in proximity but where the donor and acceptor are brought into proximity when the probe hybridized to a target sequence. This can be accomplished, for example, by placing the donor and acceptor on opposite ends of the probe and placing target complement sequences at each end of the probe where the target complement sequences are complementary to adjacent sequences in a target sequence. If the donor moiety of a fluorescent activated probe is itself a fluorescent label, it can release energy as fluorescence (typically at a different wavelength than the fluorescence of the acceptor) when not in proximity to an acceptor (that is, when the probes are not hybridized to the target sequence). When the probes hybridize to a target sequence, the overall effect would then be a reduction of donor fluorescence and an increase in acceptor fluorescence. FRET probes are an example of fluorescent activated probes.

Stem quenched primers are primers that when not hybridized to a complementary sequence form a stem structure (either an intramolecular stem structure or an intermolecular stem structure) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. In the disclosed method, stem quenched primers are used as primers for nucleic acid synthesis and thus become incorporated into the synthesized or amplified nucleic acid. Examples of stem quenched primers are peptide nucleic acid quenched primers and hairpin quenched primers.

Peptide nucleic acid quenched primers are primers associated with a peptide nucleic acid quencher or a peptide nucleic acid fluor to form a stem structure. The primer contains a fluorescent label or a quenching moiety and is associated with either a peptide nucleic acid quencher or a peptide nucleic acid fluor, respectively. This puts the fluorescent label in proximity to the quenching moiety. When the primer is replicated, the peptide nucleic acid is displaced, thus allowing the fluorescent label to produce a fluorescent signal.

Hairpin quenched primers are primers that when not hybridized to a complementary sequence form a hairpin structure (and, typically, a loop) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. Hairpin quenched primers are typically used as primers for nucleic acid synthesis and thus become incorporated into the synthesized or amplified nucleic acid. Examples of hairpin quenched primers are Amplifluor primers (Nazerenko et al., Nucleic Acids Res. 25:2516-2521 (1997)) and scorpion primers (Thelwell et al., Nucleic Acids Res. 28(19):3752-3761 (2000)).

Cleavage activated primers are similar to cleavage activated probes except that they are primers that are incorporated into replicated strands and are then subsequently cleaved. Little et al., Clin. Chem. 45:777-784 (1999), describe the use of cleavage activated primers.

Multiplexing with ARMS

In some embodiments, detection of multiple polymorphisms, insertions, deletions or other mutations is desired. In some embodiments, the primer is designed such that the base on the 3' end is over the mutation. In some embodiments, additional intentional polymorphisms are designed into the primer. In one embodiment, the presence of a probe attached to the primer allows for allele specific real-time detection of multiple polymorphisms in the same location.

Mutation Differentiation with the Probe

In some embodiments the differentiation of polymorphisms is accomplished using the capture sequence attached to the primer. In some embodiments the capture sequence has additional mutations intentionally added to improve differentiation. In some embodiments, the capture sequence will not bind when a polymorphism is present, preventing efficient amplification round after around. In some embodiments where the capture sequence has a detectable label, even if some amplification does occur, the capture sequence does not bind sufficiently to generate a detectable signal.

RNA and Other Reactions

In some embodiments, a polymerase other than a DNA polymerase is used. A variety of polymerases and enzymes capable of adding one or more bases to a nucleic acid template are known to those skilled in the art. In some embodiments, reverse transcription is desired. In some embodiments, the probe has a sufficiently low melting temperature that the polymerase can extend underneath it. In other embodiments, an increase in the temperature after a time for initial polymerization removes the capture sequence from the template, allowing the polymerase to extend. In other embodiments, additional primer sequences are used that do not have a capture sequence, allowing the polymerase to make copies in an uninhibited fashion at lower reaction temperatures.

Target Nucleic Acid Molecules

Nucleic acid molecules, which are the object of amplification, can be any nucleic acid from any source. In general, the disclosed method is performed using a nucleic acid sample that contains (or is suspected of containing) nucleic acid molecules to be amplified.

A nucleic acid sample can be any nucleic acid sample of interest. The source, identity, and preparation of many such nucleic acid samples are known. It is preferred that nucleic acid samples known or identified for use in amplification or detection methods be used for the method described herein. The nucleic acid sample can be, for example, a nucleic acid sample from one or more cells, tissue, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy aspiration, and archeological samples such as bone or mummified tissue. Types of useful nucleic acid samples include blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, a crude cell lysate samples, forensic samples, archeological samples, infection samples, nosocomial infection samples, production samples, drug preparation samples, biological molecule production samples, protein preparation samples, lipid preparation samples, and/or carbohydrate preparation samples.

For whole genome amplification, preferred nucleic acid samples are nucleic acid samples from a single cell. The nucleic acid samples for use in the disclosed method are preferably nucleic acid molecules and samples that are complex and non-repetitive. Where the nucleic acid sample is a genomic nucleic acid sample, the genome can be the genome from any organism of interest. For example, the genome can be a viral genome, a bacterial genome, a eubacterial genome, an archae bacterial genome, a fungal genome, a microbial genome, a eukaryotic genome, a plant genome, an animal genome, a vertebrate genome, an invertebrate genome, an insect genome, a mammalian genome, or a human genome. The target genome is preferably pure or substantially pure, but this is not required. For example, a genomic sample from an animal source may include nucleic acid from contaminating or infecting organisms.

The nucleic acid sample can be, or can be derived from, for example, one or more whole genomes from the same or different organisms, tissues, cells or a combination; one or more partial genomes from the same or different organisms, tissues, cells or a combination; one or more whole chromosomes from the same or different organisms, tissues, cells or a combination; one or more partial chromosomes from the same or different organisms, tissues, cells or a combination; one or more chromosome fragments from the same or different organisms, tissues, cells or a combination; one or more artificial chromosomes; one or more yeast artificial chromosomes; one or more bacterial artificial chromosomes; one or more cosmids; or any combination of these.

Oligonucleotide Synthesis

Primers, detection probes, address probes, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method. Solid phase chemical synthesis of DNA fragments is routinely performed using protected nucleoside cyanoethyl phosphoramidites (S. L. Beaucage et al. (1981) Tetrahedron Lett. 22:1859). In this approach, the 3'-hydroxyl group of an initial 5'-protected nucleoside is first covalently attached to the polymer support (R. C. Pless et al. (1975) Nucleic Acids Res. 2:773 (1975)). Synthesis of the oligonucleotide then proceeds by deprotection of the 5'-hydroxyl group of the attached nucleoside, followed by coupling of an incoming nucleoside-3'-phosphoramidite to the deprotected hydroxyl group (M. D. Matteucci et a. (1981) J. Am. Chem. Soc. 103:3185). The resulting phosphite triester is finally oxidized to a phosphorotriester to complete the internucleotide bond (R. L. Letsinger et al. (1976) J. Am. Chem. Soc. 9:3655). Alternatively, the synthesis of phosphorothioate linkages can be carried out by sulfurization of the phosphite triester. Several chemicals can be used to perform this reaction, among them 3H-1,2-benzodithiole-3-one, 1,1-dioxide (R. P. Iyer, W. Egan, J. B. Regan, and S. L. Beaucage, J. Am. Chem. Soc., 1990, 112, 1253-1254). The steps of deprotection, coupling and oxidation are repeated until an oligonucleotide of the desired length and sequence is obtained. Other methods exist to generate oligonucleotides such as the H-phosphonate method (Hall et al, (1957) J. Chem. Soc., 3291-3296) or the phosphotriester method as described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994). Other forms of oligonucleotide synthesis are described in U.S. Pat. Nos. 6,294,664 and 6,291,669.

The nucleotide sequence of an oligonucleotide is generally determined by the sequential order in which subunits of subunit blocks are added to the oligonucleotide chain during synthesis. Each round of addition can involve a different, specific nucleotide precursor, or a mixture of one or more different nucleotide precursors. For the disclosed primers of specific sequence, specific nucleotide precursors would be added sequentially.

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807-10815 (1995), McGraw et al., *Biotechniques* 8:674-678 (1990), and Rychlik et al., *Nucleic Acids Res.* 18:6409-6412 (1990).

So long as their relevant function is maintained, primers, detection probes, address probes, and any other oligonucleotides can be made up of or include modified nucleotides (nucleotide analogs). Many modified nucleotides are known and can be used in oligonucleotides, and are disclosed elsewhere herein.

Kits

The materials described above as well as other materials can be packaged together in any suitable combination as a kit useful for performing, or aiding in the performance of, the disclosed method. It is useful if the kit components in a given kit are designed and adapted for use together in the disclosed method. For example, disclosed are kits for amplification of nucleic acid samples, the kit comprising cooperative nucleic acids and a DNA polymerase. The kits also can contain nucleotides, buffers, detection probes, fluorescent change probes, lysis solutions, stabilization solutions, denaturation solutions, or a combination.

Uses

The disclosed method and compositions are applicable to numerous areas including, but not limited to, analysis of nucleic acids present in cells (for example, analysis of genomic DNA in cells), disease detection, mutation detection, gene discovery, gene mapping (molecular haplotyping), and agricultural research. Particularly useful is whole genome amplification. Other uses include, for example, detection of nucleic acids in cells and on genomic DNA arrays; molecular haplotyping; mutation detection; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

Amplification

Amplification methods suitable for use with the present methods include, for example, polymerase chain reaction (PCR), reverse transcription PCR(RT-PCR), ligase chain reaction (LCR), transcription-based amplification system (TAS), nucleic acid sequence based amplification (NASBA) reaction, self-sustained sequence replication (3SR), strand displacement amplification (SDA) reaction, boomerang DNA amplification (BDA), Q-beta replication: or isothermal nucleic acid sequence based amplification. These methods of amplification each described briefly below and are well-known in the art.

PCR is a technique for making many copies of a specific template DNA sequence. The reaction consists of multiple amplification cycles and is initiated using a pair of primer oligonucleotides that hybridize to the 5' and 3' ends of the sequence to be copied. The amplification cycle includes an initial denaturation, and up to 50 cycles of annealing, strand elongation (or extension) and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan, et al, Journal of Clinical Microbiology, 33(3):556-561 (1995). Briefly, a PCR reaction mixture includes two specific primers, dNTPs, Taq polymerase, and 1×PCR Buffer, which is amplified using a thermal cycler. Cycling parameters can be varied, depending on, for example, the melting temperature of the primer or the length of nucleic acids to be extended. The skilled artisan is capable of designing and preparing primers that are appropriate for amplifying a target sequence. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill and include considerations described herein. For example, the length of a short nucleic acid or oligonucleotide can relate to its hybridization specificity or selectivity.

Real time PCR is PCR-based amplification method in which PCR products are detected in real time, that is, the accumulation of PCR products can be determined at each cycle. An example of Real Time PCR is performed using TaqMan probes in combination with a suitable amplification/analyzer such as Applied Biosystems (ABI) Prism 7900HT Sequence Detection System, which is a high-throughput real-time PCR system. Briefly, TaqMan probes specific for the amplified target sequence are included in the PCR amplification reaction. These probes contain a reporter dye at the 5' end and a quencher dye at the 3' end. Probes hybridizing to different target sequences are conjugated with a different fluorescent reporter dye. In this way, more than one target sequence can be assayed for in the same reaction vessel. During PCR, the fluorescently labeled probes bind specifically to their respective target sequences; the 5' nuclease activity of Taq polymerase cleaves the reporter dye from the probe and a fluorescent signal is generated. The increase in fluorescence signal is detected only if the target sequence is complementary to the probe and is amplified during PCR. A mismatch between probe and target greatly reduces the efficiency of probe hybridization and cleavage. The ABI Prism 7700HT or 7900HT Sequence detection System measures the increase in fluorescence during PCR thermal cycling, providing "real time" detection of PCR product accumulation. Real Time detection on the ABI Prism 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually.

"RT-PCR" as used herein refers to the combination of reverse transcription and PCR in a single assay. "Reverse transcription" is a process whereby an RNA template is transcribed into a DNA molecule by a reverse transcriptase enzyme. Thus, "reverse transcriptase" describes a class of polymerases characterized as RNA-dependent DNA polymerases, that is, such polymerases use an RNA template to synthesize a DNA molecule. Historically, reverse transcriptases have been used to reverse-transcribe mRNA into cDNA. However, reverse transcriptases can be used to reverse-transcribe other types of RNAs such as viral genomic RNA or viral sub-genomic RNA. Standard reverse transcriptases include Maloney Murine Leukemia Virus Reverse Transcriptase (MoMuLV RT) and Avian myoblastosis virus (AMV). These enzymes have 5'→3' RNA-dependent DNA polymerase activity, 5'→3' DNA-dependent DNA polymerase activity, and RNase H activity. However, unlike many DNA-dependent DNA polymerases, these enzymes lack 3'→5' exonuclease activity necessary for "proofreading," (i.e., correcting errors made during transcription). After a DNA copy of an RNA has been prepared, the DNA copy may be subjected to various DNA amplification methods such as PCR.

LCR is a method of DNA amplification similar to PCR, except that it uses four primers instead of two and uses the enzyme ligase to ligate or join two segments of DNA. LCR can be performed as according to Moore et al., Journal of Clinical Microbiology 36(4)1028-1031 (1998). Briefly, an LCR reaction mixture contains two pair of primers, dNTP, DNA ligase and DNA polymerase representing about 90 µl, to which is added 100 µl of isolated nucleic acid from the target organism. Amplification is performed in a thermal cycler (e.g., LCx of Abbott Labs, North Chicago, Ill.).

TAS is a system of nucleic acid amplification in which each cycle is comprised of a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., PNAS 86:1173-7 (1989). Briefly, extracted RNA is combined with TAS amplification buffer and bovine serum albumin, dNTPs, NTPs, and two oligonucleotide primers, one of which contains a PBS. The sample is heated to denature the RNA template and cooled to the primer annealing temperature. Reverse transcriptase (RT) is added the sample incubated at the appropriate temperature to allow cDNA elongation. Subsequently T7 RNA polymerase is added and the sample is incubated at 3TC for approximately 25 minutes for the synthesis of RNA. The above steps are then repeated. Alternatively, after the initial cDNA synthesis, both RT and RNA polymerase are added following a 1 minute 100° C. denaturation followed by an RNA elongation of approximately 30 minutes at 37° C. TAS can be also be performed on solid phase as according to Wylie et al., Journal of Clinical Microbiology, 36(12):3488-3491 (1998). In this method, nucleic acid targets are captured with magnetic beads containing specific capture primers. The beads with captured targets are washed and pelleted before adding amplification reagents which contains amplification primers, dNTP, NTP, 2500 U of reverse transcriptase and 2500 U of T7 RNA polymerase. A 100 µl TMA reaction mixture is placed in a tube, 200 µl oil reagent is added and amplification is accomplished by incubation at 42° C. in a waterbath for one hour.

NASBA is a transcription-based amplification method which amplifies RNA from either an RNA or DNA target. NASBA is a method used for the continuous amplification of nucleic acids in a single mixture at one temperature. For example, for RNA amplification, avian mycloblastosis virus (AMV) reverse transcriptase, RNase H and T7 RNA polymerase are used. This method can be performed as according to Heim, et al., Nucleic Acids Res., 26(9):2250-2251 (1998). Briefly, an NASBA reaction mixture contains two specific primers, dNTP, NTP, 6.4 U of AMV reverse transcriptase, 0.08 U of *Escherichia coli* Rnase H, and 32 U of T7 RNA polymerase. The amplification is carried out for 120 min at 41° C. in a total volume of 201.

In a related method, self-sustained sequence-replication (3SR) reaction, isothermal amplification of target DNA or RNA sequences in vitro using three enzymatic activities: reverse transcriptase, DNA-dependent RNA polymerase and *Escherichia coli* ribonuclease H. This method may be modified from a 3-enzyme system to a 2-enzyme system by using human immunodeficiency virus (HIV)-1 reverse transcriptase instead of avian myeloblastosis virus (AMV) reverse transcriptase to allow amplification with T7 RNA polymerase but without *E. coli* ribonuclease H. In the 2-enzyme 3SR, the amplified RNA is obtained in a purer form compared with the 3-enzyme 3SR (Gebinoga & Oehlenschlager European Journal of Biochemistry, 235: 256-261, 1996).

SDA is an isothermal nucleic acid amplification method. A primer containing a restriction site is annealed to the template. Amplification primers are then annealed to 5' adjacent sequences (forming a nick) and amplification is started at a fixed temperature. Newly synthesized DNA strands are nicked by a restriction enzyme and the polymerase amplification begins again, displacing the newly synthesized strands. SDA can be performed as according to Walker, et al., PNAS, 89:392-6 (1992). Briefly, an SDA reaction mixture contains four SDA primers, dGTP, dCTP, TTP, dATP, 150 U of Hinc II, and 5 U of exonuclease-deficient of the large fragment of *E. coli* DNA polymerase I (exo.sup.—Klenow polymerase). The sample mixture is heated 95° C. for 4 minutes to denature target DNA prior to addition of the enzymes. After addition of the two enzymes, amplification is carried out for 120 min. at 37° C. in a total volume of 50 µl. Then, the reaction is terminated by heating for 2 minutes at 95° C.

Boomerang DNA amplification (BDA) is a method in which the polymerase begins extension from a single primer-binding site and then makes a loop around to the other strand, eventually returning to the original priming site on the DNA. BDA is differs from PCR through its use of a single primer. This method involves an endonuclease digestion of a sample DNA, producing discrete DNA fragments with sticky ends, ligating the fragments to "adapter" polynucleotides (comprised of a ligatable end and first and second self-complementary sequences separated by a spacer sequence) thereby forming ligated duplexes. The ligated duplexes are denatured to form templates to which an oligonucleotide primer anneals at a specific sequence within the target or marker sequence of interest. The primer is extended with a DNA polymerase to form duplex products followed by denaturation of the duplex products. Subsequent multiple cycles of annealing, extending, and denaturing are performed to achieve the desired degree of amplification (U.S. Pat. No. 5,470,724).

The Q-beta replication system uses RNA as a template. Q-beta replicase synthesizes the single-stranded RNA genome of the coliphage Qβ. Cleaving the RNA and ligating in a nucleic acid of interest allows the replication of that sequence when the RNA is replicated by Q-beta replicase (Kramer & Lizardi Trends Biotechnol. 1991 9(2):53-8, 1991).

A variety of amplification enzymes are well known in the art and include, for example, DNA polymerase, RNA polymerase, reverse transcriptase, Q-beta replicase, thermostable DNA and RNA polymerases. Because these and other amplification reactions are catalyzed by enzymes, in a single step assay that the nucleic acid releasing reagents and the detection reagents should not be potential inhibitors of amplification enzymes if the ultimate detection is to be amplification based.

Amplification of the nucleic acid molecules in a nucleic acid sample can result replication of at least 0.01% of the nucleic acid sequences in the nucleic acid sample, at least 0.1% of the nucleic acid sequences in the nucleic acid sample, at least 1% of the nucleic acid sequences in the nucleic acid sample, at least 5% of the nucleic acid sequences in the nucleic acid sample, at least 10% of the nucleic acid sequences in the nucleic acid sample, at least 20% of the nucleic acid sequences in the nucleic acid sample, at least 30% of the nucleic acid sequences in the nucleic acid sample, at least 40% of the nucleic acid sequences in the nucleic acid sample, at least 50% of the nucleic acid sequences in the nucleic acid sample, at least 60% of the nucleic acid sequences in the nucleic acid sample, at least 70% of the nucleic acid sequences in the nucleic acid sample, at least 80% of the nucleic acid sequences in the nucleic acid sample, at least 90% of the nucleic acid sequences in the nucleic acid sample, at least 95% of the nucleic acid sequences in the nucleic acid sample, at least 96% of the nucleic acid sequences in the nucleic acid sample, at least 97% of the nucleic acid sequences in the nucleic acid sample, at least 98% of the nucleic acid sequences in the nucleic acid sample, or at least 99% of the nucleic acid sequences in the nucleic acid sample.

The various sequence representations described above and elsewhere herein can be, for example, for 1 target sequence, 2 target sequences, 3 target sequences, 4 target sequences, 5 target sequences, 6 target sequences, 7 target sequences, 8 target sequences, 9 target sequences, 10 target sequences, 11 target sequences, 12 target sequences, 13 target sequences, 14 target sequences, 15 target sequences, 16 target sequences, 17 target sequences, 18 target sequences, 19 target sequences, 20 target sequences, 25 target sequences, 30 target sequences, 40 target sequences, 50 target sequences, 75 target sequences, or 100 target sequences. The sequence representation can be, for example, for at least 1 target sequence, at least 2 target sequences, at least 3 target sequences, at least 4 target sequences, at least 5 target sequences, at least 6 target sequences, at least 7 target sequences, at least 8 target sequences, at least 9 target sequences, at least 10 target sequences, at least 11 target sequences, at least 12 target sequences, at least 13 target sequences, at least 14 target sequences, at least 15 target sequences, at least 16 target sequences, at least 17 target sequences, at least 18 target sequences, at least 19 target sequences, at least 20 target sequences, at least 25 target sequences, at least 30 target sequences, at least 40 target sequences, at least 50 target sequences, at least 75 target sequences, or at least 100 target sequences.

The sequence representation can be, for example, for 1 target sequence, 2 different target sequences, 3 different target sequences, 4 different target sequences, 5 different target sequences, 6 different target sequences, 7 different target sequences, 8 different target sequences, 9 different target sequences, 10 different target sequences, 11 different target sequences, 12 different target sequences, 13 different target sequences, 14 different target sequences, 15 different target sequences, 16 different target sequences, 17 different target sequences, 18 different target sequences, 19 different target sequences, 20 different target sequences, 25 different target sequences, 30 different target sequences, 40 different target sequences, 50 different target sequences, 75 different target sequences, or 100 different target sequences. The sequence representation can be, for example, for at least 1 target sequence, at least 2 different target sequences, at least 3 different target sequences, at least 4 different target sequences, at least 5 different target sequences, at least 6 different target sequences, at least 7 different target sequences, at least 8 different target sequences, at least 9 different target sequences, at least 10 different target sequences, at least 11 different target sequences, at least 12 different target sequences, at least 13 different target sequences, at least 14 different target sequences, at least 15 different target sequences, at least 16 different target sequences, at least 17 different target sequences, at least 18 different target sequences, at least 19 different target sequences, at least 20 different target sequences, at least 25 different target sequences, at least 30 different target sequences, at least 40 different target sequences, at least 50 different target sequences, at least 75 different target sequences, or at least 100 different target sequences.

Detection

Products of amplification can be detected using any nucleic acid detection technique. For real-time detection, the amplification products and the progress of amplification are detected during amplification. Real-time detection is usefully accomplished using one or more or one or a combination of fluorescent change probes and fluorescent change primers. Other detection techniques can be used, either alone or in combination with real-timer detection and/or detection involving fluorescent change probes and primers. Many techniques are known for detecting nucleic acids. The nucleotide sequence of the amplified sequences also can be determined using any suitable technique.

For example, nucleic acid product may be detected by any of a variety of well-known methods, for example, electrophoresis (e.g., gel electrophoresis or capillary electrophoresis). Amplified fragments may be subjected to further methods of detecting, for example, variant sequences (e.g., single nucleotide polymorphisms (SNPs)). An exemplary method is single nucleotide primer extension (Lindblad-Toh et al., Large-scale discovery and genotyping of single-nucleotide polymorphisms in the mouse. Nature Genet. 2000 April; 24(4):381-6). In this reaction, an oligonucleotide primer is designed to have a 3' end that is one nucleotide 5' to a specific mutation site. In some embodiments, the extension primers are labeled with a tag or a member of a binding pair to allow the capture of the primer on solid phase. In particular embodiments, the primers may be tagged with varying lengths of nonspecific polynucleotides (e.g., poly-GACT) to allow multiplex detection of preferably 2 or more, more preferably 3 or more, 4 or more, 5 or more, even 10 or more different mutations (polymorphisms) in a single reaction. The primer hybridizes to the PCR amplicon in the presence of one or more labeled ddNTPs and a DNA polymerase. The polymerase extends the primer by one nucleotide, adding a single, labeled ddNTP to the 3' end of the extension primer. The addition of a dideoxy nucleotide terminates chain elongation. If more than one dideoxynucleotide (e.g., ddATP, ddGTP, ddCTP, ddTTP, ddUTP, etc.) is used in a reaction, one or more can be labeled. If multiple labels are used, the labels can be distinguishable e.g., each is labeled with a different fluorescent colored dye. The products are labeled oligonucleotides, each one of which may be detected based on its label. Further methods of detecting variant sequences include the READIT SNP Genotyping System (Promega Corporation, Madison Wis.) and oligonucleotide ligation assays.

EXAMPLES

Example 1: CoPrimers (Cooperative Nucleic Acids)

Disclosed herein is the use of CoPrimers for mutation and SNP genotyping, mainly for single-nucleotide variants. As genotyping assays are often performed as a multiplex, POC included evaluation of CoPrimer-based genotyping assays in both monoplex and multiplex settings. Performance of CoPrimer genotyping assays while mixed and matched in any combination was also assessed.

Several candidate positions were considered, under both Priming and Capture sequence. The mismatch placement under the Capture sequence did not yield very consistent allelic differentiation and this approach was abandoned early during our POC experiments. Three more promising approaches involved positioned the variant-induced mismatch under the Priming sequence. These three scenarios are depicted in FIG. 2.

Capture: Second Nucleic Acid Sequence of Co-Primer

When variant-induced mismatch was placed under the capture sequence, the dCt values (demonstrating the differentiation power of allele-specific CoPrimers) were very variable, averaging at 8 cycles with standard deviation of 4.8 cycles (FIG. 15; all mismatches are in lower case). In several cases, the "matched" Ct values (WT-matching CoPrimer amplifying WT template) were very high—meaning, the PCR was very inefficient.

Priming: First Nucleic Acid Sequence of Co-Primer

Large number of designs with variant-induced mismatch under the priming sequence were tested. Mismatch was placed under the ultimate base of the priming sequence (in FIG. 14, marked as "−1"), penultimate (−2) and antepenultimate (−3). Also, the variant-induced mismatch was combined with one or more additional (intentional) mismatches: ultimate and penultimate (−1 & −2), penultimate and antepenultimate (−2 & −3), and any of the above (−1, −2, −3 etc. . . . ) with additional 3 or 4 mismatches placed under the 5' end of the priming sequence. FIG. 14 summarizes results for all the scenarios.

With variant-induced mismatch under the ultimate base of the priming sequence (−1), very good differentiation was observed, with an average dCt value of 12 cycles ±2.8 (standard deviation). The matched Ct values were very low as well, indicating the PCR was of high efficiency.

Variant-induced mismatch located under the penultimate base of the priming sequence (−2), very good differentiation was observed, with an average dCt value of 12 cycles ±2.4. The matched Ct values were very low as well, indicating the PCR was of high efficiency.

With variant-induced mismatch under the antepenultimate base of the priming sequence (−3), intermediate differentiation was observed, with an average dCt value of 9 cycles ±3.9 (SD). The matched Ct values were very low as well, indicating the PCR exhibited high efficiency.

When variant-induced mismatch was placed under the ultimate base of the priming sequence, and additional mismatch was intentionally placed on the penultimate base (−1 & −2), modest dCt values were observed, while the matched Ct values were very high (inefficient PCR).

Variants induced mismatch on the penultimate base with additional, intentional mismatch on the antepenultimate base (−2 & −3) resulted in high matched Ct values (inefficient PCR) and variable dCt values.

Addition of multiple intentional mismatches to −1, −2, −2 & −3, −3, −3 & −4 scenarios resulted in good allelic differentiation (dCt values), but high/very high matched Ct values (inefficient PCR).

Figure 2A:
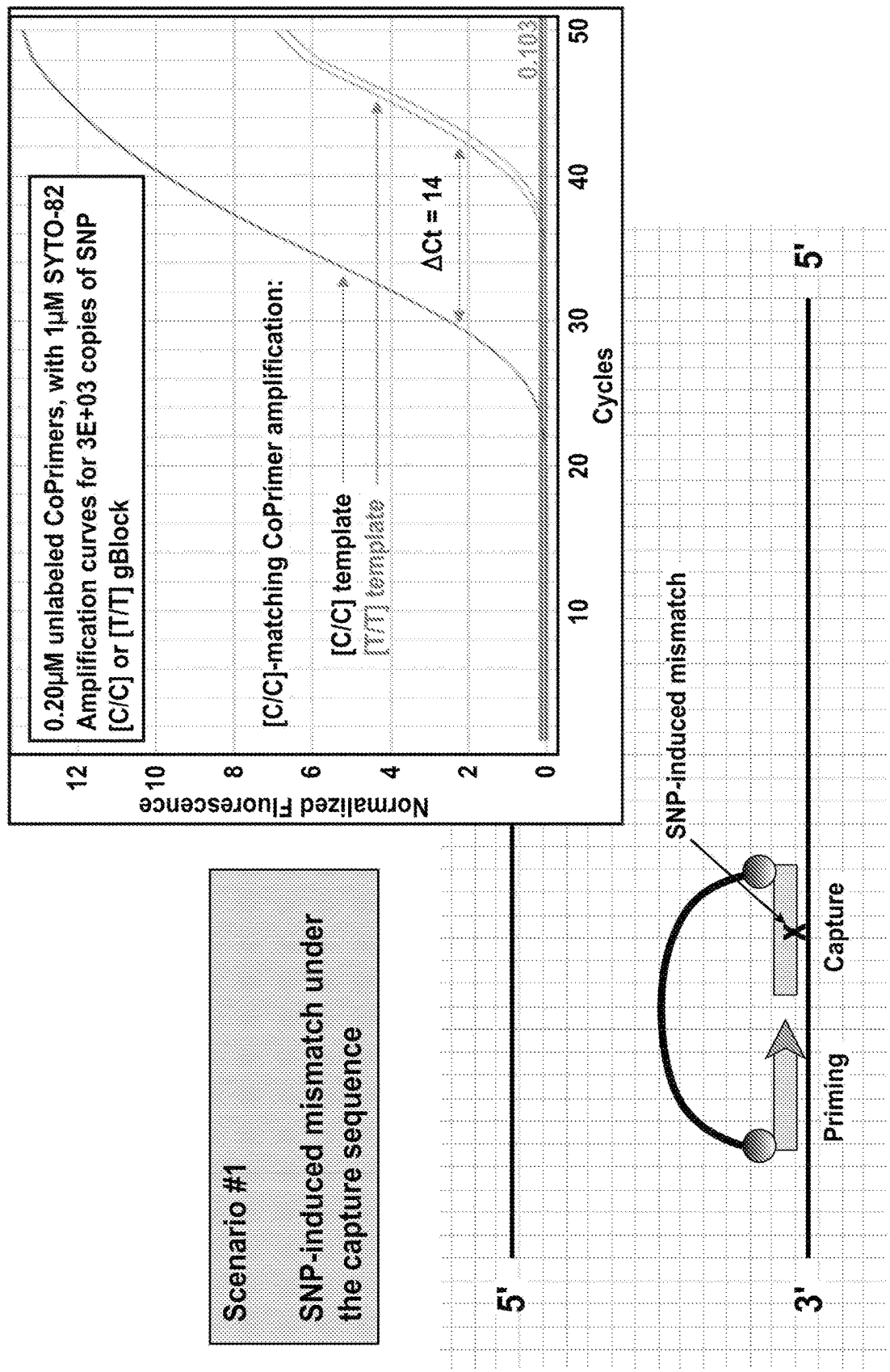
FIG. 2A-D shows approaches involving positioning the variant-induced mismatch under the priming and the capture sequence, as well as several possibilities of intentional mismatches that correspond to neither the target nor the differing nucleic acid strain.
Figure 2B:
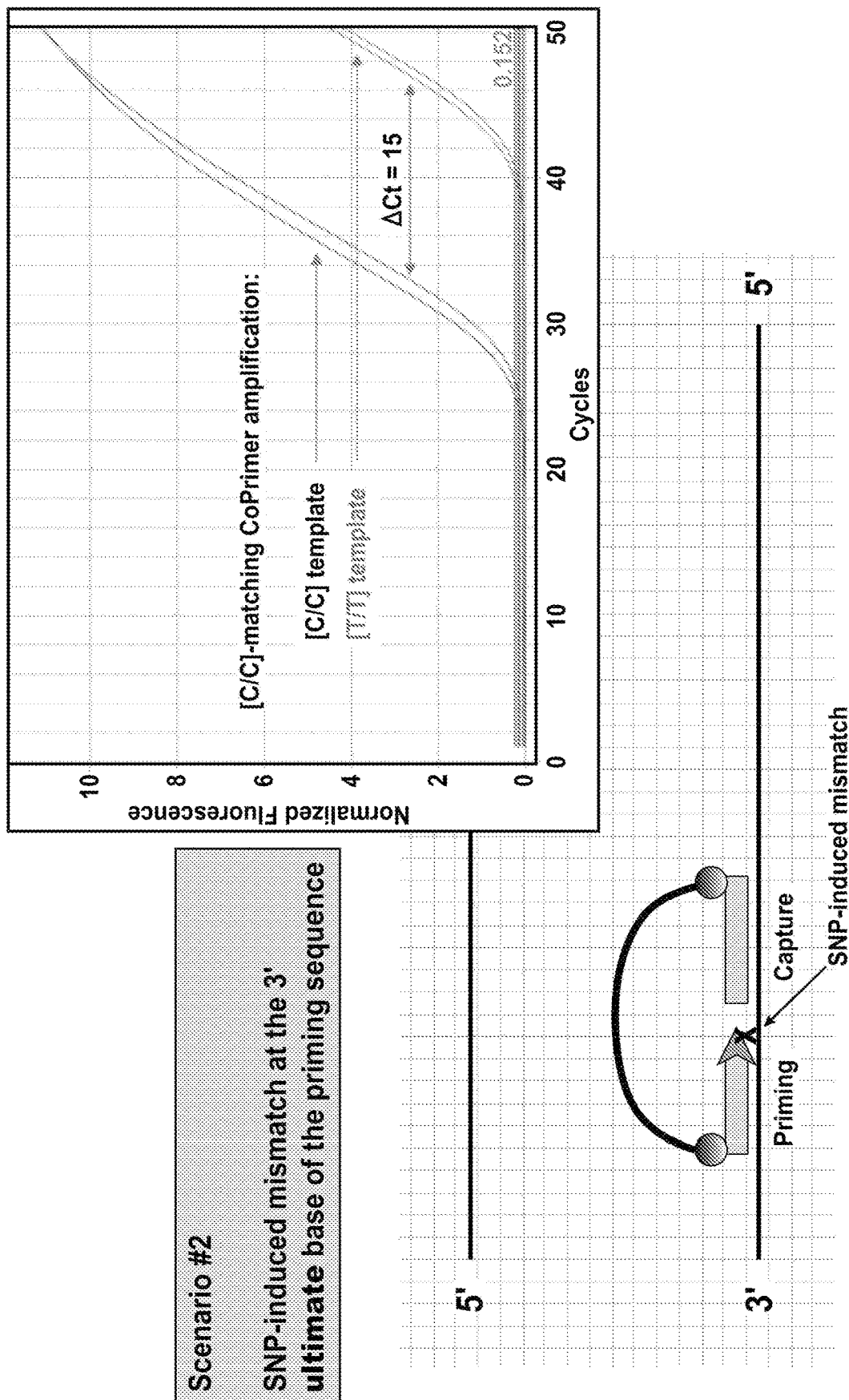
Figure 2C:
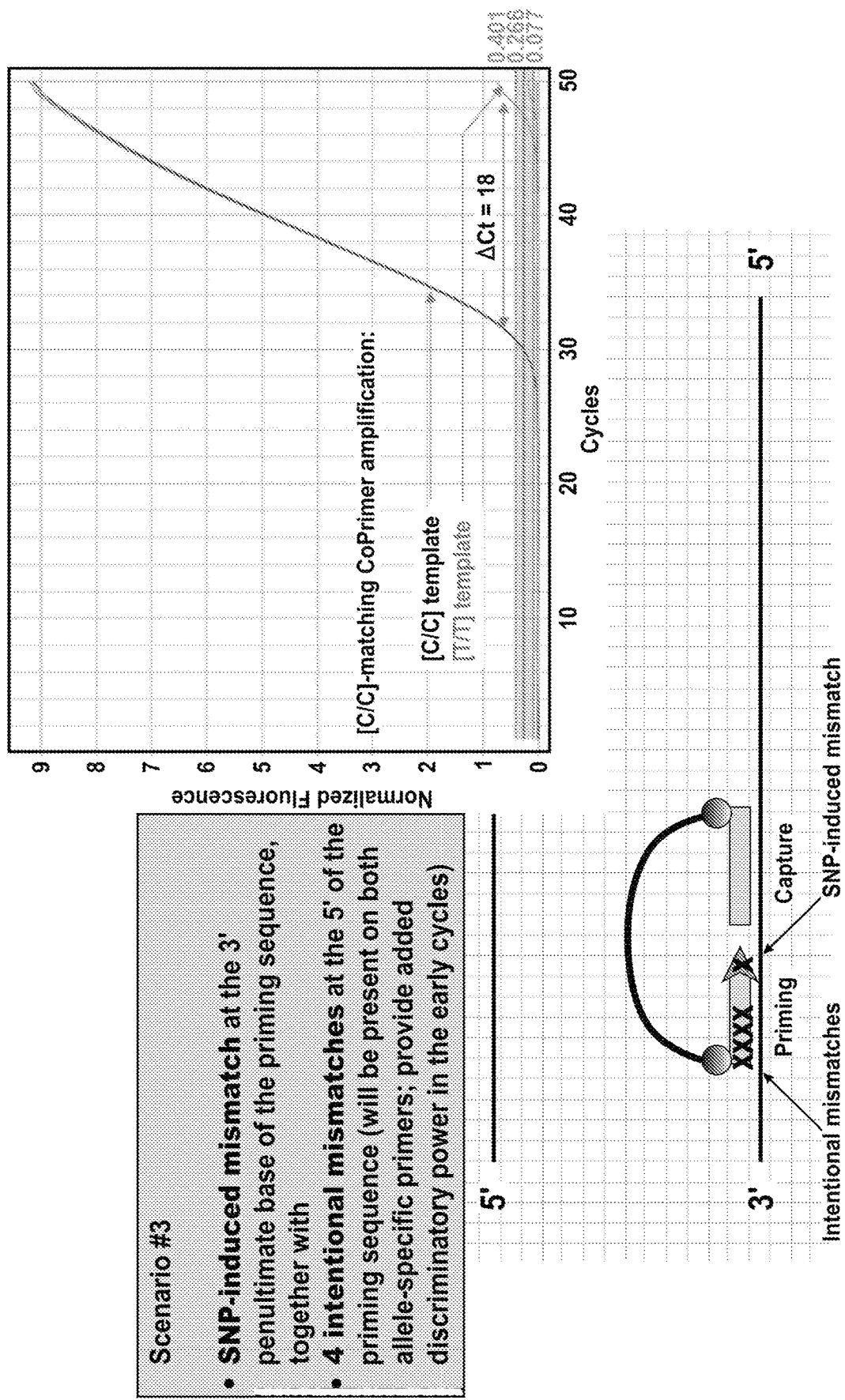
Figure 2D:
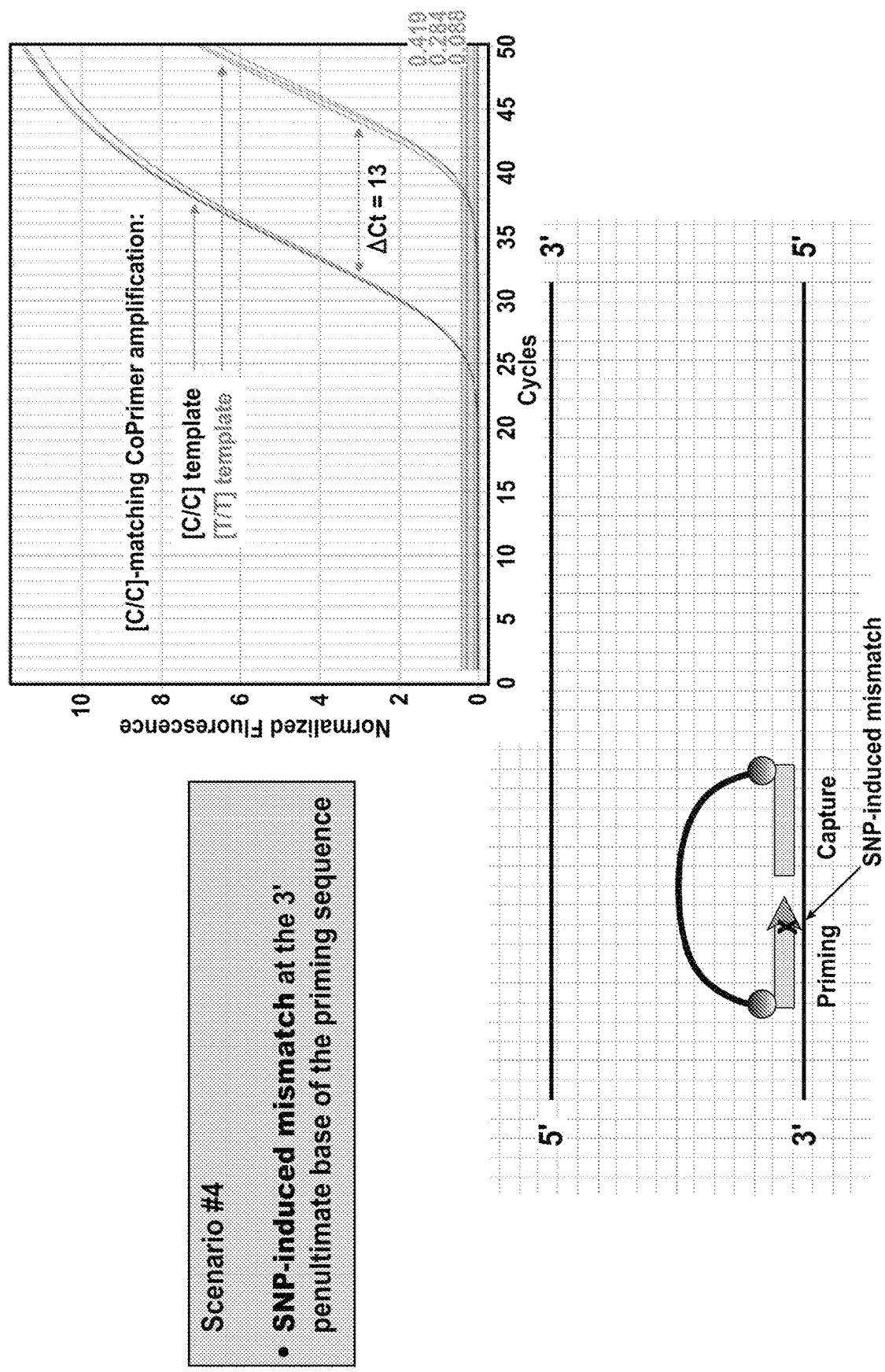
Figure 3A:
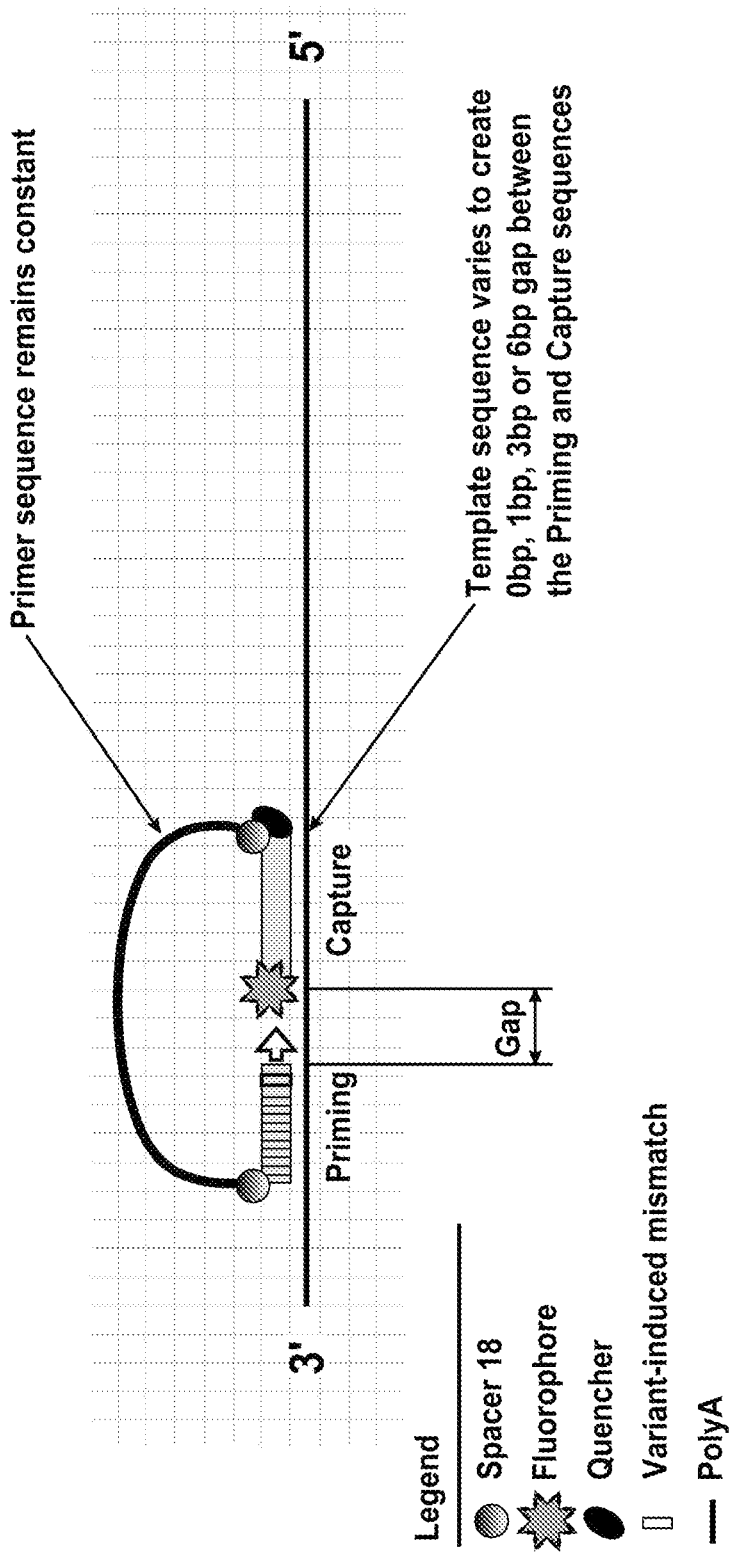
FIG. 3A-C shows gap-size studies using 0, 1, 3, or 6 nucleotide gap between the first and second sequence of the cooperative nucleic acid.
Figure 3B:
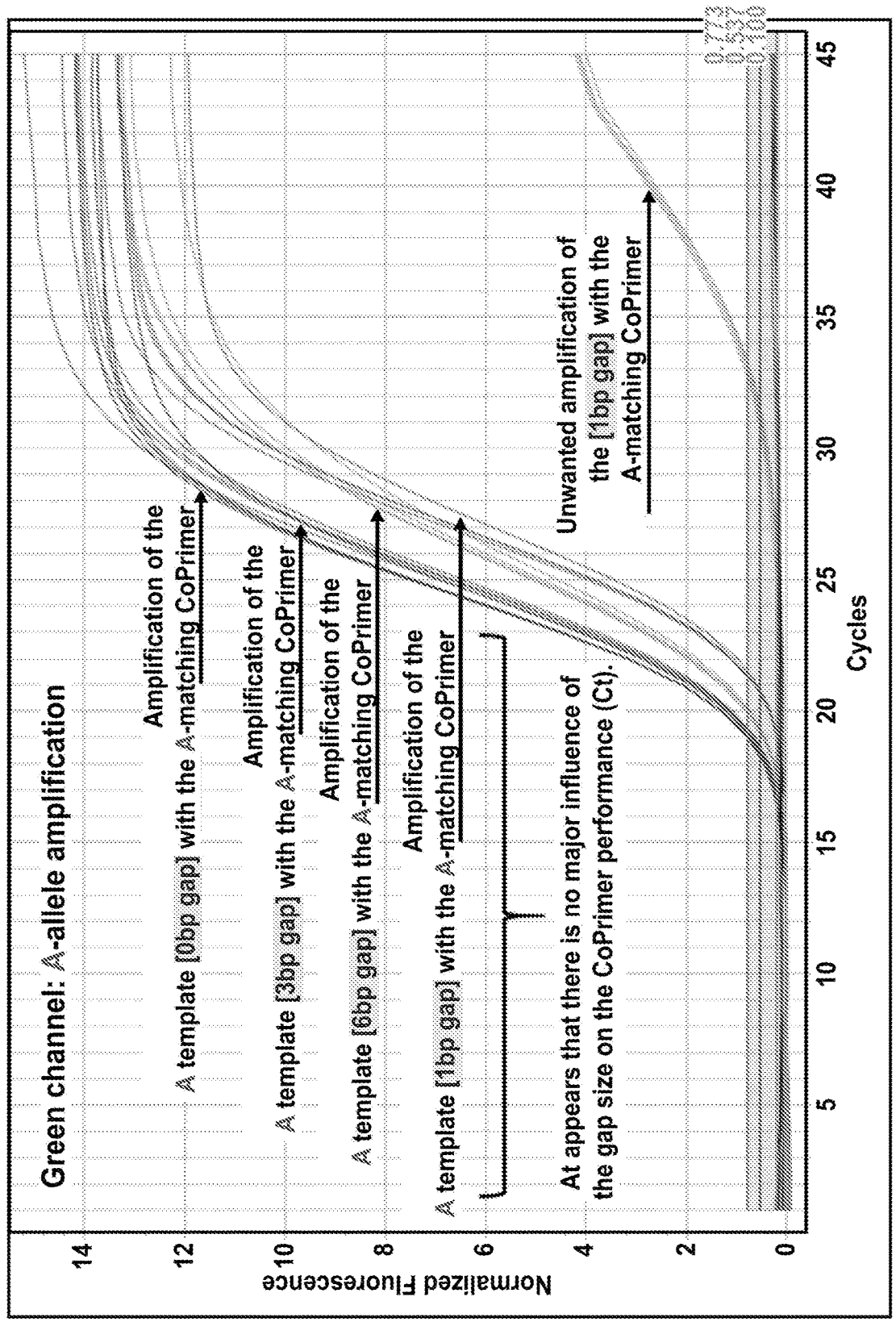
Figure 3C:
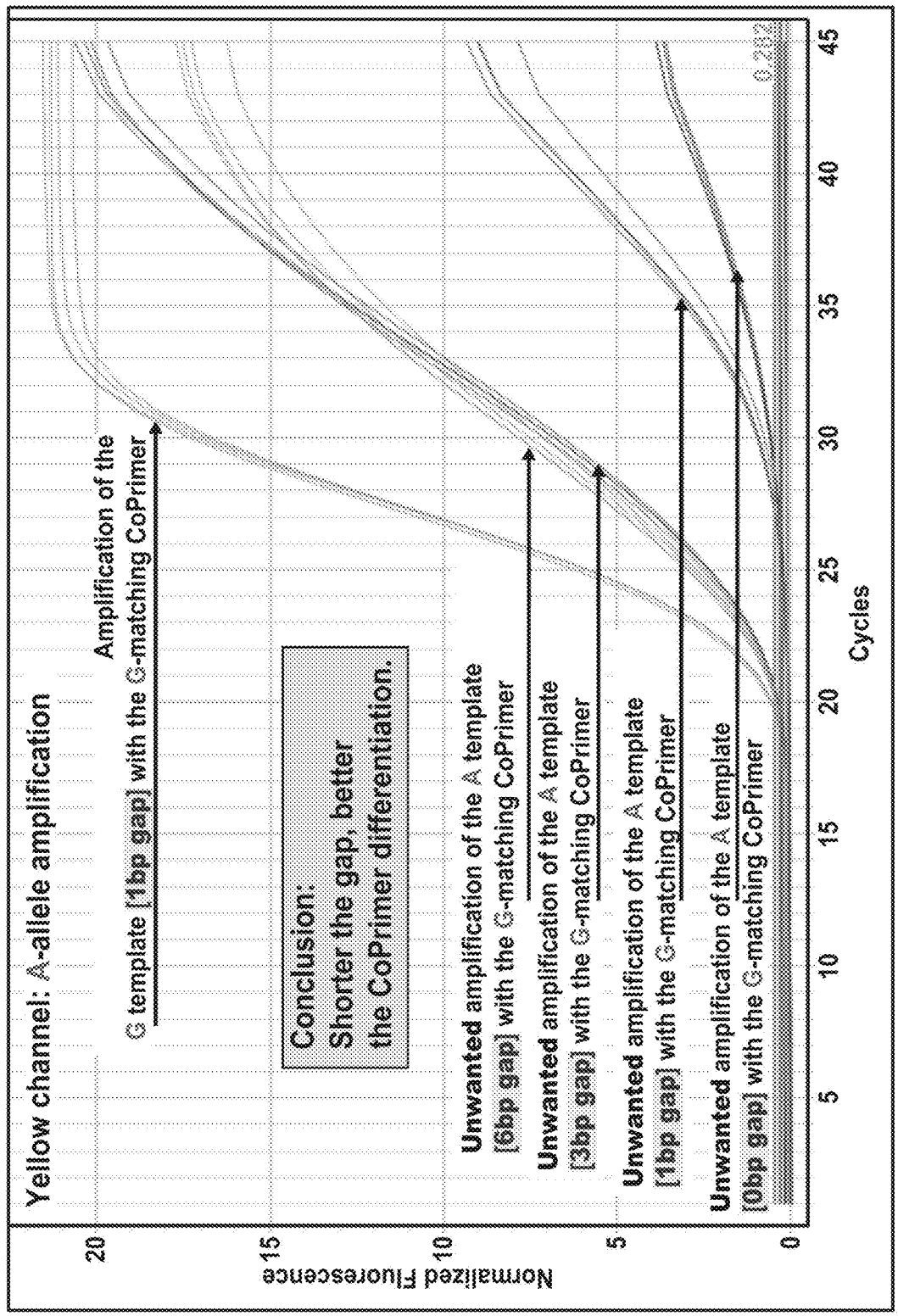
Figure 5A:
Figure 6:
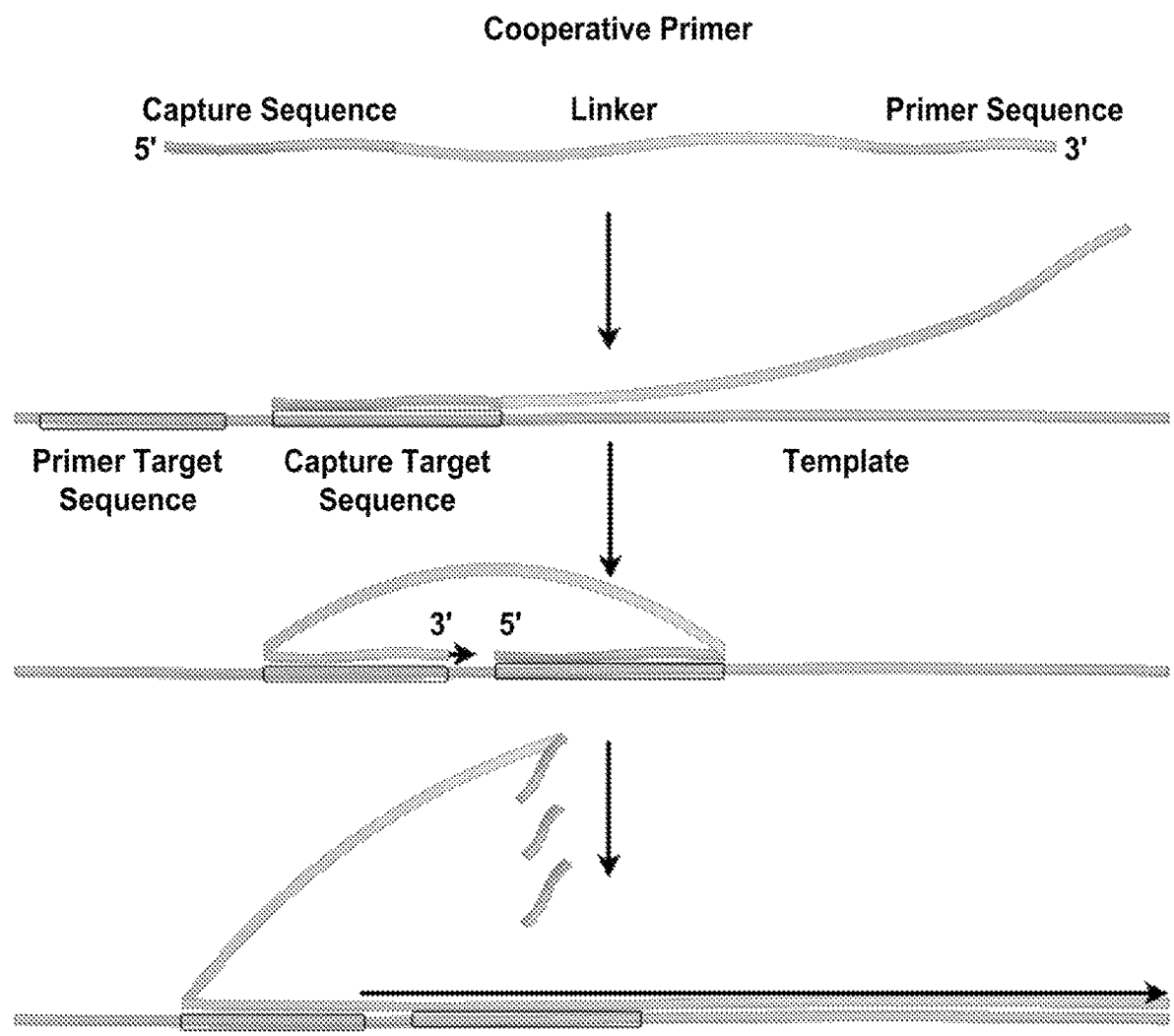
FIG. 6 shows the method of extension of a Cooperative Primer. In step 1, a Cooperative Primer is shown in solution with the capture sequence, flexible linker, and primer sequence, oriented in a 5' to 3' direction. In step 2, the capture sequence hybridizes to its target, bringing the primer into artificially close proximity to its target. The Primer Target Sequence and Capture Target Sequence are labeled. In step 3, the primer hybridizes to its target and the polymerase begins to extend. In step 4, the polymerase extends through the capture sequence, cleaving it. Note that alternatively the polymerase may extend through the capture sequence, displacing it.
Figure 7:
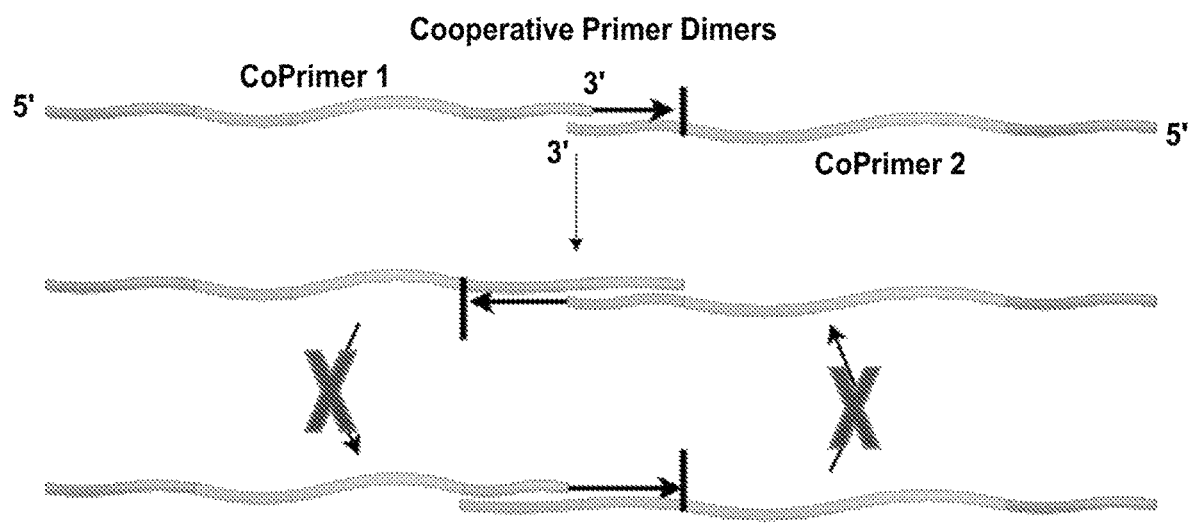
FIG. 7 shows the effect of coprimers (referred to herein as cooperative primers or cooperative nucleic acids) on primer-dimer: In step 1, two CoPrimers interact such that polymerase extends across one primer and forms a primer dimer. Extension is blocked from continuing beyond the 5' end of the primer by a non-extendable moiety. In step 2, a CoPrimer is shown binding to a primer dimer resulting in polymerase extension the other direction. In step 3, the process repeats with more primer dimers forming. Because the Tm of the primer is below reaction temperature, and extension of primer dimers past the 5' end of the primer is blocked, primer dimers formed by CoPrimers are not able to consistently bind and extend more primers. Steps 2 and 3 are unable to happen at high efficiency, noted by the red X's between them. Amplification and propagation of primer dimers is significantly restricted even if they do happen to form.

Multiple CoPrimer designs for several variants showed that the Scenario #1 (variant-induced mismatch on the 3' penultimate base of the Priming sequence, FIG. 2D yields most consistent discriminatory power (dCt; FIG. 15).

Example 2: Optimization of Gap Length

Influence of the gap length on the discriminatory power of CoPrimers was investigated. While not decreasing the PCR efficiency, a no gap (absence of a gap, 0 nucleotides) significantly improves the allele specificity of CoPrimers (see FIG. 3A-C).

Example 3: Evaluation of the Genotyping Assay PCR Efficiency while Monoplexing and Multiplexing Assays were comparably robust whether ran as a monoplex, duplex, or quadruplex (with regard to the SNP; double that for number of primer pairs in the reaction, as each SNP requires 2 FWD CoPrimers and one REV). For robustness evaluation, Table 1.

TABLE 1

MONOPLEXING VS. MULTIPLEXING EFFICIENCY-
SYNTHETIC DNA TEMPLATES FOR AMPIFICATION
EFFICIENCY VS. MULTIPLEXING EVALUATION

SNP 1 (T) CoPrimer labeled with FAM; 0.1 µM final concentration
SNP 1 (C) CoPrimer Labeled wth CAL Fluor Orange560; 0.1 µM
SNP 1 common Rev CoPrimer, unlabeled, 0.2 µM
SNP 2 (G) CoPrimer labeled with CAL Fluor Red610; 0.1 µM
SNP 2 (A) CoPrimer labeled with Quasar 670; 0.1 µM
SNP 2 common Rev CoPrimer, unlabeled 0.2 µM
SNP 3 (G) CoPrimer unlabeled 0.2 µM (double the concentration)*
SNP 3 Rev CoPrimer; 0.2 µM
SNP 4 (A) CoPrimer unlabeled; 0.2 uM (double the concentration)**
SNP 4 Rev CoPrimer; 0.2 µM
PCR Conditions:

1XBHQ Master Mix
95° C. for 15 min (polymerase activation) 1 cycle
95° C. for 15 seconds; 57° C. for 60 seconds 45 cycles
PCR templates:

SNP 1 heterozygous synthetic gBlock DNA template at a concentration of 3 + 03 copies/µl (final)
SNP 2 heterozygous synthetic gBlock DNA template at a concentration of 3 + 03 copies/µl (final)

TABLE 1-continued

MONOPLEXING VS. MULTIPLEXING EFFICIENCY-
SYNTHETIC DNA TEMPLATES FOR AMPIFICATION
EFFICIENCY VS. MULTIPLEXING EVALUATION

SNP 3 homozygous synthetic gBlock DNA template at a concentration of 3 + 03 copies/µl (final)
SNP 4 homozygous synthetic gBlock DNA template at a concentration of 3 + 03 copies/µl (final)

*Only G allele-specific CoPrimers and G-allele template were available at the time
**Only A allele-specific CoPrimers and A-allele template was available at the time Example 4: Evaluation of the Assay Performance while Mixing Various SNP Assays in Multiplex Fashion The ability to "Mix and Match" is a very important feature of any PCR genotyping technology. Below are the results of a Mix and Match Study, which allowed genotyping results to be obtained for 6 SNPs, mixed in all possible combinations (fluorophore-permitting). CoPrimers (referred to herein as cooperative nucleic acids or cooperative primers) perform well no matter what is the combination in each duplex PCR (and FIGS. 5A-D).

It will be apparent to those skilled in the art that various modifications and variations can be made in the present disclosure without departing from the scope or spirit of the invention. Other embodiments of the disclosure will be apparent to those skilled in the art from consideration of the specification and practice of the methods disclosed herein. It is intended that the specification and examples be considered as exemplary only, with a true scope and spirit of the invention being indicated by the following claims.

What is claimed is:
1. A method of synthesizing a target nucleic acid preferentially relative to a nucleic acid with one or more nucleotides that differ from the target nucleic acid, the method comprising:
   a. exposing a cooperative nucleic acid molecule to a solution suspected of comprising a target nucleic acid and also potentially comprising a nucleic acid with one or more nucleotides that differ from the target nucleic acid (differing nucleic acid), wherein the cooperative nucleic acid molecule comprises, from 3' to 5':
      i. a first nucleic acid sequence, wherein the first nucleic acid sequence is complementary to a first region of the target nucleic acid, and further wherein a penultimate nucleotide of the 3' end of the first nucleic acid sequence is complementary to the target nucleic acid, but is not complementary to the differing nucleic acid, and yet further wherein the first nucleic acid is extendable on the 3' end;
      ii. a linker connecting said first nucleic acid sequence and a second nucleic acid sequence in a manner that allows both the said first and second nucleic acid sequences to hybridize to the target nucleic acid at the same time;
      iii. the second nucleic acid sequence, wherein the second nucleic acid sequence is complementary to a second region of the target nucleic acid, wherein the complementarity between the second nucleic acid sequence and the second region of the target nucleic acid starts within one nucleotide or less of the first region of the target nucleic acid, such that it hybridizes to the second target nucleic acid downstream from the 3' end of the first nucleic acid sequence, or overlaps on a 5' end of the second nucleic acid sequence with the 3' end of the first nucleic acid sequence;
b. providing conditions appropriate for nucleic acid synthesis wherein a polymerase extends from the 3' end of the first nucleic acid sequence through the second nucleic acid sequence, thereby synthesizing the target nucleic acid preferentially to the differing nucleic acid if it is present in the solution.

2. The method of claim 1, wherein the target nucleic acid and differing nucleic acid differ by one nucleotide and wherein the one differing nucleotide comprises a single nucleotide polymorphism (SNP).

3. The method of claim 1, wherein the target nucleic acid and the differing nucleic acid differ by two nucleotides.

4. The method of claim 1, wherein the complementarity between the second nucleic acid sequence and the second region of the target nucleic acid is either within one nucleotide of the first region of the target nucleic acid, or is contiguous so that there are no gaps between where the first nucleic acid sequence hybridizes and the second nucleic acid sequence hybridizes, or is overlapping so that there is a negative gap between where the first nucleic acid sequence hybridizes and the second nucleic acid sequence hybridizes, and further wherein the overlap is one nucleotide in length, or more than one nucleotide in length.

5. The method of claim 1, wherein a second cooperative nucleic acid molecule is exposed simultaneously with the cooperative nucleic acid molecule of claim 1 to a solution comprising the differing nucleic acid and the target nucleic acid, wherein said second cooperative nucleic acid molecule targets the differing nucleic acid for amplification, such that the penultimate nucleotide of the 3' end of the first sequence of the second cooperative nucleic acid molecule is complementary to the differing nucleic acid, but is not complementary to the target nucleic acid.

6. The method of claim 5, wherein the first and second cooperative nucleic acid molecules can amplify their intended targets under substantially similar conditions.

7. The method of claim 5, wherein one or more additional differing nucleic acids are present in the solution.

8. The method of claim 7, wherein the one or more additional differing nucleic acids differ at a same nucleotide position as the target and first differing nucleic acid or the additional differing nucleic acids differ at different nucleotide positions than the target nucleic acid and a second differing nucleic acid.

9. The method of claim 8, wherein where the one or more additional differing nucleic acids differ at a same nucleotide position as the target and first differing nucleic acid, the one or more additional differing nucleic acids have different nucleotides at the same nucleotide position as the target nucleic acid and the first differing nucleic acid.

10. The method of claim 7, wherein three or more cooperative nucleic acid molecules are simultaneously exposed to the target and differing nucleic acids.

11. The method of claim 1, wherein hybridization of the first nucleic acid sequence of the cooperative nucleic acid molecule is conditional upon hybridization of the second nucleic acid sequence to the target nucleic acid.

12. The method of claim 1, wherein the cooperative nucleic acid molecule comprises a label.

13. The method of claim 12, wherein the label is a fluorescent label.

14. The method of claim 13, wherein the molecule further comprises a quencher.

15. The method of claim 1, wherein the target nucleic acid and the differing nucleic acid differ due to a deletion, addition, or substitution of a nucleotide.

* * * * *